United States Patent
Hoshi et al.

(10) Patent No.: US 12,371,684 B2
(45) Date of Patent: *Jul. 29, 2025

(54) BETA-GALACTOSIDASE ENZYMES

(71) Applicant: AMANO ENZYME INC., Nagoya (JP)

(72) Inventors: Yukiko Hoshi, Kakamigahara (JP);
Masamichi Okada, Kakamigahara (JP);
Akio Horii, Kakamigahara (JP);
Masayuki Hojo, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/503,526

(22) Filed: Nov. 7, 2023

(65) Prior Publication Data

US 2024/0084278 A1   Mar. 14, 2024

Related U.S. Application Data

(63) Continuation of application No. 17/961,625, filed on Oct. 7, 2022, now Pat. No. 11,859,222, which is a continuation of application No. 16/065,400, filed as application No. PCT/JP2016/089001 on Dec. 27, 2016, now Pat. No. 11,512,299.

(30) Foreign Application Priority Data

Dec. 29, 2015  (JP) ................. 2015-257705

(51) Int. Cl.
| | |
|---|---|
| C12N 9/38 | (2006.01) |
| C07H 3/06 | (2006.01) |
| C12N 1/21 | (2006.01) |
| C12N 5/10 | (2006.01) |
| C12N 15/09 | (2006.01) |
| C12P 19/00 | (2006.01) |
| C12P 19/14 | (2006.01) |

(52) U.S. Cl.
CPC ............ *C12N 9/2471* (2013.01); *C07H 3/06* (2013.01); *C12N 5/10* (2013.01); *C12N 15/09* (2013.01); *C12P 19/00* (2013.01); *C12P 19/14* (2013.01); *C12Y 302/01023* (2013.01)

(58) Field of Classification Search
None
See application file for complete search history.

(56) References Cited

U.S. PATENT DOCUMENTS 5,294,546 A   3/1994   Dombou et al.

FOREIGN PATENT DOCUMENTS

| JP | 1985-251896 A | 12/1985 |
| JP | 1994-002057 A | 5/1987 |
| JP | S62-111685 A | 5/1987 |
| JP | 1991-216185 A | 9/1991 |
| JP | 1993-236981 A | 9/1993 |
| JP | 1995-236480 A | 9/1995 |
| JP | H08-256730 A | 10/1996 |
| JP | 2003-325166 A | 11/2003 |

OTHER PUBLICATIONS

Gosling et al., Recent advances refining galactooligosaccharide production from lactose, Food Chem. 121, 2010, 307-18. (Year: 2010).*
Ohtsuka et al., Purification and Properties of a beta-Galactosidase with High Galactosyl Transfer Activity from Cryptococcus laurentii OKN-4, J. Ferment. Bioeng. 70, 1990, 301-07. (Year: 1990).*
Chochchaisawasdee et al., Synthesis of Galacto-oligosaccharide From Lactose Using beta-Galactosidase From Kluyveromyces lactis, Biotechnol. Bioeng. 89, 2005, 434-43. (Year: 2005).*
Ferreira Paim, K. et al., "Phylogenetic Analysis of Phenotypically Characterized Cryptococcus laurentii Isolates Reveals High Frequency of Cryptic Species," PLOS One, 2014, vol. 9, No. 9, e108633, pp. 1-16. (cited in the ISR).
International Search Report mailed Apr. 4, 2017, issued for PCT/JP2016/089001.
K. Ohtsuka et al., "Purification and Properties of a Beta-Galactosidase with High Galactosyl Transfer Activity from Cryptococcus laurentii OKN-4", Journal of Fermentation and Bioengineering, vol. 70, No. 5, Jan. 1, 1990, pp. 301-307. (cited in the Jul. 15, 2019 Search Report issued for EP16881800.3).
Database XP002792556 UniProt [Online] Oct. 5, 2010 (Oct. 5, 2010), "SubName: Full=Glycoside hydrolase family 1 protein {ECO:0000313:EMBL:EFJ00109.1}; Flags: Fragment;" retrieved from EBI accession No. UNIPROT:D8PVX2 Database accession No. D8PVX2 *sequence * (cited in the Jul. 15, 2019 Search Report issued for EP16881800.3).
Supplementary European Search Report mailed Jul. 15, 2019, issued for European Patent Application No. 16881800.3.
Office Action mailed Jun. 1, 2021, issued for Japanese Patent Application No. 2017-559227.
Von Heijne, The signal peptide, J. Membrane Biol. 115, 1990, 195-201. (Year: 1990).
Petersen et al., SignalP 4.0, Nature Methods 8, 2011, 785-86. (Year: 2011).
Nath et al., Production, purification, characterization, immobilization, and application of beta-galactosidase: a review, Asia-Pac. J Chem. Eng., 2014, DOI: 10.1002/apj.1801. (Year: 2014).
Ishikawa et al., Identification, Cloning, and Characterization of a Sporobolomyces singularis beta-Galactosidase-like Enzyme Involved in Galacto-Oligosaccharide Production, J. Biosci. Bioeng. 99, 2005. 331-39. (Year: 2005).
Genbank, Accession No. AB126324.1, 2008, www.ncbi.nlm.gov <http://www.ncbi.nlm.gov>. (Year: 2008).
Genbank, Accession No. BCD33911.1, 2020, ncbi.nlm.nih.gov <http://ncbi.nlm.nih.gov>. (Year: 2020).

(Continued)

*Primary Examiner* — Todd M Epstein
(74) *Attorney, Agent, or Firm* — Troutman Pepper Locke LLP

(57) ABSTRACT

The present invention has a purpose of providing a β-galactosidase enzyme useful for the production of oligosaccharides. Disclosed is a β-galactosidase enzyme comprising the amino acid sequence of any one of SEQ ID NOs: 1 to 4 or an amino acid sequence that is 80% or more identical to said amino acid sequence.

10 Claims, 11 Drawing Sheets

Specification includes a Sequence Listing.

(56) References Cited

OTHER PUBLICATIONS

Genbank, Accession No. LC085434.1, 2020, ncbi.nlm.nih.gov <http://ncbi.nlm.nih.gov>. (Year: 2020).

Ke et al., Toxicological evaluation of beta-galactosidase enzyme produced by Papiliotrema terrestris, Regulatory Toxicol. Pharmacol., 2018, 92, 213-19.

Crestani et al., *Cryptococcus terrestris* sp. nov., a tremellaceous, anamorphic yeast phylogenetically related to Cryptococcus flavescens, Int. J. System. Evolutionary Microbiol., 59, 2009, 631-36.

Yurkov et al., Multigene Assessment of the Species Boundaries and Sexual Status of the Basidiomycetous Yeasts Cryptococcus flavescens and C. terrestris (Tremellales), PLOS One, Mar. 2015, 10(3), e0120400.

Chen et al., Production, Purification, and Characterization of a Potential Thermostable Galactosidase for Milk Lactose Hydrolysis from Bacillus stearothermophilus, J. Dairy Sci., 91, 2008, 1751-1758.

Recombinant DNA. (1992), In C. G. Morris (Ed.), Academic Press Dictionary of Science and Technology (4th ed.), Elsevier Science & Technology. (Year: 1992).

\* cited by examiner

| Enzyme | Reaction temperature | Amount of GOS (%) | Ratio in GOS (%) | | |
|---|---|---|---|---|---|
| | | | ≧ DP4 | DP3 | DP2 (Lac not included) |
| WT strain enzyme | 65°C | 53.4 | 22.1 | 51.8 | 26.1 |
| | 70°C | 54.2 | 25.8 | 47.4 | 26.8 |

Fig. 6

| Strain (enzyme) | Ratio in GOS (%) | | |
|---|---|---|---|
| | ≧ DP4 | DP3 | DP2 (Lac not included) |
| Cryptococcus laurentii | 18.0 | 55.8 | 26.1 |
| Sporobolomyces singularis | 13.5 | 54.5 | 32.0 |
| Cryptococcus terrestris MM13-F2171 (WT strain enzyme) | 16.7 | 57.5 | 25.8 |

| Strain (enzyme) | Ratio in DP3 (%) | | |
|---|---|---|---|
| | β1-4 | β1-6 | β1-2, β1-3 |
| Cryptococcus laurentii | 71.9 | 12.0 | 16.1 |
| Sporobolomyces singularis | 70.1 | 5.7 | 24.3 |
| Cryptococcus terrestris MM13-F2171 (WT strain enzyme) | 76.3 | 1.5 | 22.1 |

Fig. 7

| Enzyme | Reaction temperature | Amount of GOS (%) | Ratio in GOS (%) | | |
|---|---|---|---|---|---|
| | | | ≧ DP4 | DP3 | DP2 (Lac not included) |
| Cryptococcus terrestris M6 (Mutant strain enzyme 3) | 50°C | 46.9 | 6.4 | 68.9 | 24.7 |
| | 60°C | 52.1 | 16.1 | 58.2 | 25.8 |
| | 65°C | 53.2 | 20.9 | 53.4 | 26.0 |
| | 70°C | 53.9 | 24.5 | 49.2 | 26.3 |

*Fig. 9*

| Strain (enzyme) | Ratio in GOS (%) | | |
|---|---|---|---|
| | ≧ DP4 | DP3 | DP2 (Lac not included) |
| Cryptococcus laurentii | 18.0 | 55.8 | 26.1 |
| Sporobolomyces singularis | 13.5 | 54.5 | 32.0 |
| Cryptococcus terrestris M2 (Mutant strain enzyme 1) | 14.2 | 60.5 | 25.3 |
| Cryptococcus terrestris M6 (Mutant strain enzyme 3) | 19.9 | 54.2 | 25.8 |

| Strain (enzyme) | Ratio in DP3 (%) | | |
|---|---|---|---|
| | β1-4 | β1-6 | β1-2, β1-3 |
| Cryptococcus laurentii | 71.9 | 12.0 | 16.1 |
| Sporobolomyces singularis | 70.1 | 5.7 | 24.3 |
| Cryptococcus terrestris M2 (Mutant strain enzyme 1) | 79.0 | 0.4 | 20.7 |
| Cryptococcus terrestris M6 (Mutant strain enzyme 3) | 75.2 | 2.7 | 22.1 |

*Fig. 10*

SEQUENCE LISTING

```
Sequence total quantity: 16
SEQ ID NO: 1              moltype = AA   length = 696
FEATURE                   Location/Qualifiers
source                    1..696
                          mol_type = protein
                          note = Cryptococcus terrestris
                          organism = Cryptococcus terrestris
SEQUENCE: 1
MIPASALLAA VPLLAQQVSA GILRRQNAAG SDSAAPDSIA DASTGVVSSI ATEAVSSGAT    60
GLVASVAMSF ASSMATPTAT VTGLSSETGA PSNTPMASAS GSVPTTTSAV GSGDFDWVQT   120
DGLPTITTTL ATTNQDAITP TATGPVGGQG TPAVNFTDYS SSSLEQFWND WVGEVEEPPF   180
AYVPEPPNPY PLPNAPPPIY PEYYTKRPKD ILPDYKFPKD FLFGWATAAQ QWEGAVKADG   240
KGPSIWDWAS RFPGFIADNT TSDVGDLGYY LYKEDLARIA ALGANVYSFS MFWTRIFPFG   300
KADSPVNQAG IDFYHDLIDY SWSLGIEPVV TLFHWDTPLA LQLEYGGFAS ERIIDDYVNY   360
AETVFKAYNG SVHKWVTFNE PVVFCSQMAA PVNTTLPPNL NSTIYPYTCS YHLVLAHAKT   420
VKRFRELNIQ GQIAFKSDNF VGIPWREGNQ EDIDAVERHQ AYQIGIFAEP IYNTGDWPDI   480
VKNDLSPDIL PRFTDDEIAM IKCTADFFPI DGYRDGYVQA VPGGVEACVA NISNPLWPAC   540
NQVNFYDSTP AGWAIGTFGN WPTTPWLQNT WQFVRPFLAD LAKRYPTEGG IYLSEFGFSE   600
PFENDKTFIY QITQDSGRTA YFNSYLGEVL KGIVEDGIPI KGVFGWSMVD NFEWNSGLST   660
RFGVQYVDYN SPTRQRTFKR SALEMSEFWN AHRCSA                            696

SEQ ID NO: 2              moltype = AA   length = 566
FEATURE                   Location/Qualifiers
source                    1..566
                          mol_type = protein
                          note = Cryptococcus terrestris
                          organism = Cryptococcus terrestris
SEQUENCE: 2
ATTNQDAITP TATGPVGGQG TPAVNFTDYS SSSLEQFWND WVGEVEEPPF AYVPEPPNPY    60
PLPNAPPPIY PEYYTKRPKD ILPDYKFPKD FLFGWATAAQ QWEGAVKADG KGPSIWDWAS   120
RFPGFIADNT TSDVGDLGYY LYKEDLARIA ALGANVYSFS MFWTRIFPFG KADSPVNQAG   180
IDFYHDLIDY SWSLGIEPVV TLFHWDTPLA LQLEYGGFAS ERIIDDYVNY AETVFKAYNG   240
SVHKWVTFNE PVVFCSQMAA PVNTTLPPNL NSTIYPYTCS YHLVLAHAKT VKRFRELNIQ   300
GQIAFKSDNF VGIPWREGNQ EDIDAVERHQ AYQIGIFAEP IYNTGDWPDI VKNDLSPDIL   360
PRFTDDEIAM IKCTADFFPI DGYRDGYVQA VPGGVEACVA NISNPLWPAC NQVNFYDSTP   420
AGWAIGTFGN WPTTPWLQNT WQFVRPFLAD LAKRYPTEGG IYLSEFGFSE PFENDKTFIY   480
QITQDSGRTA YFNSYLGEVL KGIVEDGIPI KGVFGWSMVD NFEWNSGLST RFGVQYVDYN   540
SPTRQRTFKR SALEMSEFWN AHRCSA                                       566

SEQ ID NO: 3              moltype = AA   length = 560
FEATURE                   Location/Qualifiers
source                    1..560
                          mol_type = protein
                          note = Cryptococcus terrestris
                          organism = Cryptococcus terrestris
SEQUENCE: 3
AITPTATGPV GGQGTPAVNF TDYSSSSLEQ FWNDWVGEVE EPPFAYVPEP PNPYPLPNAP    60
PPIYPEYYTK RPKDILPDYK FPKDFLFGWA TAAQQWEGAV KADGKGPSIW DWASRFPGFI   120
ADNTTSDVGD LGYYLYKEDL ARIAALGANV YSFSMFWTRI FPFGKADSPV NQAGIDFYHD   180
LIDYSWSLGI EPVVTLFHWD TPLALQLEYG GFASERIIDD YVNYAETVFK AYNGSVHKWV   240
TFNEPVVFCS QMAAPVNTTL PPNLNSTIYP YTCSYHLVLA HAKTVKRFRE LNIQGQIAFK   300
SDNFVGIPWR EGNQEDIDAV ERHQAYQIGI FAEPIYNTGD WPDIVKNDLS PDILPRFTDD   360
EIAMIKCTAD FFPIDGYRDG YVQAVPGGVE ACVANISNPL WPACNQVNFY DSTPAGWAIG   420
TFGNWPTTPW LQNTWQFVRP FLADLAKRYP TEGGIYLSEF GFSEPFENDK TFIYQITQDS   480
GRTAYFNSYL GEVLKGIVED GIPIKGVFGW SMVDNFEWNS GLSTRFGVQY VDYNSPTRQR   540
TFKRSALEMS EFWNAHRCSA                                              560

SEQ ID NO: 4              moltype = AA   length = 555
FEATURE                   Location/Qualifiers
source                    1..555
                          mol_type = protein
                          note = Cryptococcus terrestris
                          organism = Cryptococcus terrestris
SEQUENCE: 4
ATGPVGGQGT PAVNFTDYSS SSLEQFWNDW VGEVEEPPFA YVPEPPNPYP LPNAPPPIYP    60
EYYTKRPKDI LPDYKFPKDF LFGWATAAQQ WEGAVKADGK GPSIWDWASR FPGFIADNTT   120
SDVGDLGYYL YKEDLARIAA LGANVYSFSM FWTRIFPFGK ADSPVNQAGI DFYHDLIDYS   180
WSLGIEPVVT LFHWDTPLAL QLEYGGFASE RIIDDYVNYA ETVFKAYNGS VHKWVTFNEP   240
VVFCSQMAAP VNTTLPPNLN STIYPYTCSY HLVLAHAKTV KRFRELNIQG QIAFKSDNFV   300
GIPWREGNQE DIDAVERHQA YQIGIFAEPI YNTGDWPDIV KNDLSPDILP RFTDDEIAMI   360
KCTADFFPID GYRDGYVQAV PGGVEACVAN ISNPLWPACN QVNFYDSTPA GWAIGTFGNW   420
PTTPWLQNTW QFVRPFLADL AKRYPTEGGI YLSEFGFSEP FENDKTFIYQ ITQDSGRTAY   480
FNSYLGEVLK GIVEDGIPIK GVFGWSMVDN FEWNSGLSTR FGVQYVDYNS PTRQRTFKRS   540
ALEMSEFWNA HRCSA                                                   555

SEQ ID NO: 5              moltype = DNA   length = 2091
FEATURE                   Location/Qualifiers
source                    1..2091
```

```
                        mol_type = other DNA
                        note = Cryptococcus terrestris
                        organism = Cryptococcus terrestris
SEQUENCE: 5
atgatcccgg caagtgcact ccttgccgcc gtaccctcc ttgcccaaca ggtgagcgcc    60
ggcatactgc gaagacagaa tgctgcgggt tcggattcgg cagcgcctga ctcgatcgcg   120
gatgcgtcca ccggtgtcgt ctcgtcgatc gccacggaag ccgtctcttc gggagcgaca   180
ggccttgtcg cgtccgtcgc catgtcattc gcctcgtcga tggcgactcc aacgccaca    240
gtgacgggcc taagctccga gacgggagcg ccttccaaca ccccaatggc cagtgcctct   300
ggtagtgtcc ctacaaccac ctctgccgtc gggtctggcg acttcgactg ggtccagaca   360
gacggcctgc ccacgatcac gaccactttg gctactacga accaggacgc aatcactccg   420
acggcgacgg gccccgtcgg cggacagggc acccctgctg tcaacttcac cgactactct   480
tcatcgtcgc tcgagcagtt ttggaacgac tgggtgggag aggtggagga ccgccgttc   540
gcctacgtcc cggaaccgcc taacccgtac ccgttaccga acgccccgcc tccaatctac   600
cccgagtact acaccaagcg tcccaaggac attctccccg actacaagtt ccccaaagac   660
ttcctgtttg gctgggcgac cgccgcgcag cagtgggagg gggccgtcaa ggcggatggg   720
aaggggccgt ccatctggga ctgggccagc cggttcccgg ggttcattgc ggacaacacg   780
acttccgacg tcggagactt gggatactat ttatacaaag aggacctcgc taggatcgct   840
gcattgggcg caaacgttta ctctttcagc atgttctgga cacgatctt tcccttcggc    900
aaggccgact cgcctgtcaa tcaagcgggc atcgacttct accacgactt gatcgattat   960
tcttggagcc tgggcatcga gcccgtcgtg acattgttcc attgggatac gccgctcgcc  1020
ctccagcttg agtacggagg tttcgccagc gagcgaatca ttgatgacta cgtcaactat  1080
gcggaaaccg tgttcaaggc gtacaacggt agtgtgcaca aatgggtcac attcaacgag  1140
cctgtggtgt tctgcagcca gatggcagcg cccgtgaaca ctactctacc gccgaacctc  1200
aactcgacaa tctaccccta tacctgcagc tatcacctcg tgctagccca cgccaagacg  1260
gtcaagcggt tcagggagtt gaacattcag ggccagatcg cttttcaagtc ggacaattt   1320
gtcggtatcc cgtggcgtga ggggaaccaa gaggacatag atgcggtcga gcgccatcag  1380
gcgtaccaga tcgggatctt tgctgagccg atctacaaca ccggagactg gcccgatatc  1440
gtgaagaatg atctctcccc cgacatcctt cctcgattca cggatgacga gatcgcgatg  1500
atcaagtgca ctgccgactt cttcccccatc gatggctaca gggacggtta tgtccaggct  1560
gtaccggggg gtgtcgaagc ttgcgtcgcg aacatcagca acccgctttg gcctgcttgc  1620
aaccaagtca acttctatga ttccacaccc gccggatggg cgatcggcac gttcggcaac  1680
tggccgacga caccctggct ccagaacacc tggcagtttg tgcgcccctt cctgctgat   1740
ctggcaaagc ggtaccccac cgaaggcggc atctaccttt cggaatttgg cttctccgag  1800
ccgttcgaaa atgataaaac cttcatttac cagatcaccc aggacagcgg acggacggcg  1860
tacttcaaca gttacctcgg cgaagtgttg aaaggtatcg ttgaagatgg cattcctatc  1920
aagggcgtgt tcggctggag tatggtcgac aactttgaat ggaactctgg cttgtctact  1980
cgcttcgcg tccaatacgt tgattacaac agcccgacgc gtcaacgaac gttcaagcgg  2040
tccgctctgg agatgagcga gttctggaat gctcatcgat gttccgccta a           2091

SEQ ID NO: 6             moltype = DNA   length = 1701
FEATURE                  Location/Qualifiers
source                   1..1701
                         mol_type = other DNA
                         note = Cryptococcus terrestris
                         organism = Cryptococcus terrestris
SEQUENCE: 6
gctactacga accaggacgc aatcactccg acggcgacgg gccccgtcgg cggacagggc    60
acccctgctg tcaacttcac cgactactct tcatcgtcgc tcgagcagtt ttggaacgac   120
tgggtgggag aggtggagga ccgccgttc gcctacgtcc cggaaccgcc taacccgtac   180
ccgttaccga acgccccgcc tccaatctac cccgagtact acaccaagcg tcccaaggac   240
attctccccg actacaagtt ccccaaagac ttcctgtttg gctgggcgac cgccgcgcag   300
cagtgggagg gggccgtcaa ggcggatggg aaggggccgt ccatctggga ctgggccagc   360
cggttcccgg ggttcattgc ggacaacacg acttccgacg tcggagactt gggatactat   420
ttatacaaag aggacctcgc taggatcgct gcattgggcg caaacgttta ctctttcagc   480
atgttctgga cacgatctt tcccttcggc aaggccgact cgcctgtcaa tcaagcgggc   540
atcgacttct accacgactt gatcgattat tcttggagcc tgggcatcga gcccgtcgtg   600
acattgttcc attgggatac gccgctcgcc ctccagcttg agtacggagg tttcgccagc   660
gagcgaatca ttgatgacta cgtcaactat gcggaaaccg tgttcaaggc gtacaacggt   720
agtgtgcaca aatgggtcac attcaacgag cctgtggtgt tctgcagcca gatggcagcg   780
cccgtgaaca ctactctacc gccgaacctc aactcgacaa tctaccccta tacctgcagc   840
tatcacctcg tgctagccca cgccaagacg gtcaagcggt tcagggagtt gaacattcag   900
ggccagatcg cttttcaagtc ggacaattt gtcggtatcc cgtggcgtga ggggaaccaa   960
gaggacatag atgcggtcga gcgccatcag gcgtaccaga tcgggatctt tgctgagccg  1020
atctacaaca ccggagactg gcccgatatc gtgaagaatg atctctcccc cgacatcctt  1080
cctcgattca cggatgacga gatcgcgatg atcaagtgca ctgccgactt cttcccccatc  1140
gatggctaca gggacggtta tgtccaggct gtaccggggg gtgtcgaagc ttgcgtcgcg  1200
aacatcagca acccgctttg gcctgcttgc aaccaagtca acttctatga ttccacaccc  1260
gccggatggg cgatcggcac gttcggcaac tggccgacga caccctggct ccagaacacc  1320
tggcagtttg tgcgcccctt cctgctgat ctggcaaagc ggtaccccac cgaaggcggc   1380
atctaccttt cggaatttgg cttctccgag ccgttcgaaa atgataaaac cttcatttac  1440
cagatcaccc aggacagcgg acggacggcg tacttcaaca gttacctcgg cgaagtgttg  1500
aaaggtatcg ttgaagatgg cattcctatc aagggcgtgt tcggctggag tatggtcgac  1560
aactttgaat ggaactctgg cttgtctact cgcttcgcg tccaatacgt tgattacaac   1620
agcccgacgc gtcaacgaac gttcaagcgg tccgctctgg agatgagcga gttctggaat  1680
gctcatcgat gttccgccta a                                             1701

SEQ ID NO: 7             moltype = DNA   length = 1683
FEATURE                  Location/Qualifiers
```

| source | 1..1683 |
| --- | --- |
| | mol_type = other DNA |
| | note = Cryptococcus terrestris |
| | organism = Cryptococcus terrestris |

SEQUENCE: 7
```
gcaatcactc cgacggcgac gggcccgtc ggcggacagg gcacccctgc tgtcaacttc    60
accgactact cttcatcgtc gctcgagcag ttttggaacg actgggtggg agaggtggag   120
gagccgccgt tcgcctacgt cccggaaccg cctaacccgt acccgttacc gaacgccccg   180
cctccaatct accccgagta ctacaccaag cgtcccaagg acattctccc cgactacaag   240
ttccccaaag acttcctgtt tggctgggcg accgccgcgc agcagtggga ggggccgtc    300
aaggcggatg ggaaggggcc gtccatctgg gactgggcca gccggttccc ggggttcatt   360
gcggacaaca cgacttccga cgtcggagac ttgggatact atttatacaa agaggacctc   420
gctaggatcg ctgcattggg cgcaaacgtt tactctttca gcatgttctg gacacggatc   480
ttttcccttcg gcaaggccga ctcgcctgtc aatcaagcgg catcgactt ctaccacgac   540
ttgatcgatt attcttggag cctgggcatc gagcccgtcg tgacattgtt ccattgggat   600
acgccgctcg ccctccagct tgagtacgga ggtttcgcca gcgagcgaat cattgatgac   660
tacgtcaact atgcggaaac cgtgttcaag gcgtacaacg tagtgtgca caaatgggtc    720
acattcaaga agcctgtggt gttctgcagc cagatgcgac cgcccgtgaa cactactcta   780
ccgccgaacc tcaactcgac aatctacccc tatacctgca gctatcacct cgtgctagcc   840
cacgccaaga cggtcaagcg gttcaggag ttgaacattc agggccagat cgcttttcaag    900
tcggacaatt ttgtcggtat cccgtggcgt gaggggaacc aagaggacat agatgcggtc   960
gagcgccatc aggcgtacca gatcgggatc tttgctgagc catctacaa caccggagac  1020
tggcccgata tcgtgaagaa tgatctctcc cccgacatcc ttcctcgatt caccggatgac  1080
gagatcgcga tgatcaagtg cactgccgac ttcttcccca tcgatggcta cagggacggt  1140
tatgtccagg ctgtaccggg gggtgtcgaa gcttgcgtcg cgaacatcag caacccgctt  1200
tggcctgctt gcaaccaagt caacttctat gattccaac ccgccggatg ggcgatcggc   1260
acgttcggca actggccgac gacacccgg ctccagaaca cctggcagtt tgtgcgcccc   1320
ttcctcgctg atctggcaaa gcggtacccc accgaaggcg gcatctacct ttcggaatt   1380
ggcttctccg agccgttcga aaatgataaa accttcattt accagatcac ccaggacagc  1440
ggacggacgg cgtacttcaa cagttacctc ggcgaagtgt tgaaaggtat cgttgaagat  1500
ggcattccta tcaagggcgt gttcggctgg agtatggtcg acaactttga atggaactct  1560
ggcttgtcta ctcgcttcgg cgtccaatac gttgattaca cagcccgac gcgtcaacga   1620
acgttcaagc ggtccgctct ggagatgagc gagttctgga atgctcatcg atgttccgcc  1680
taa                                                                1683
```

| SEQ ID NO: 8 | moltype = DNA  length = 1668 |
| --- | --- |
| FEATURE | Location/Qualifiers |
| source | 1..1668 |
| | mol_type = other DNA |
| | note = Cryptococcus terrestris |
| | organism = Cryptococcus terrestris |

SEQUENCE: 8
```
gcgacgggcc ccgtcggcgg acagggcacc cctgctgtca acttcaccga ctactcttca    60
tcgtcgctcg agcagttttg gaacgactgg gtgggagagg tggaggagcc gccgttcgcc   120
tacgtcccgg aaccgcctaa cccgtacccg ttaccgaacg cccccgcctcc aatctacccc   180
gagtactaca ccaagcgtcc caaggacatt ctccccgact acaagttccc caaagacttc   240
ctgtttggct gggcgaccgc cgcgcagcag tgggagggg cgtcaaggc ggatgggaag    300
gggccgtcca tctgggactg gccagccgg ttcccggggt tcattgcgga caacacgact   360
tccgacgtcg gagacttggg atactattta tacaaagagg acctcgctag gatcgctgca   420
ttgggcgcaa acgtttactc tttcagcatg ttctggacac ggatctttcc cttcggcaag   480
gccgactcgc ctgtcaatca agcgggcatc gacttctacc acgacttgat cgattattct   540
tggagcctgg gcatcgagcc cgtcgtgaca ttgttccatt gggatacgcc gctcgccctc   600
cagcttgagt acgaggtttt cgccagcgag cgaatcattg atgactacgt caactatgcg   660
gaaaccgtgt tcaaggcgta caacggtagt gtgcacaaat gggtcacatt caacgagcct   720
gtggtgttct gcagccagat ggcagcgccc gtgaacacta ctctaccgcc gaacctcaac   780
tcgacaatct accctatac ctgcagctat cacctcgtgc tagcccacgc caagacggtc   840
aagcggttca ggagttgaa cattcagggc cagatcgctt tcaagtcgga caattttgtc   900
ggtatcccgt ggcgtgaggg gaaccaagag gacatagatg cggtcgagcg ccatcaggcg  960
taccagatcg ggatctttgc tgagccgatc tacaaccgga gactggcc cgatatcgtg  1020
aagaatgatc tctcccccga catccttcct cgattcaccg atgacgagat cgcgatgatc  1080
aagtgcactg ccgacttctt ccccatcgat ggctacaggg acggttatgt ccaggctgta  1140
ccggggggtg tcgaagcttg cgtcgcgaac atcagcaacc cgctttggcc tgcttgcaac  1200
caagtcaact tctatgattc cacacccgcc ggatgggcga tcggcacgtt cggcaactgg  1260
ccgacgacac cctggctcca gaacacctgg cagtttgtgc gccccttcct cgctgatctg  1320
gcaaagcggt accccaccga aggcggcatc tacctttcgg aatttggctt ctccgagccg  1380
ttcgaaaatg ataaaacctt catttaccag atcacccagg acagcggacg gacggcgtac  1440
ttcaacagtt acctcggcga agtgttgaaa ggtatcgttg aagatggcat tcctatcaag  1500
ggcgtgttcg gctggagtat ggtcgacaac tttgaatgga ctctggctt gtctactcgc  1560
ttcggcgtcc aatacgttga ttacaacagc ccgacgcgtc aacgaacgtt caagcggtcc  1620
gctctggaga tgagcgagtt ctggaatgct catcgatgtt ccgcctaa              1668
```

| SEQ ID NO: 9 | moltype = AA  length = 11 |
| --- | --- |
| FEATURE | Location/Qualifiers |
| source | 1..11 |
| | mol_type = protein |
| | note = Cryptococcus terrestris |
| | organism = Cryptococcus terrestris |

SEQUENCE: 9
GVQYVDYNSP T                                                        11

```
SEQ ID NO: 10              moltype = AA   length = 11
FEATURE                    Location/Qualifiers
source                     1..11
                           mol_type = protein
                           note = Cryptococcus terrestris
                           organism = Cryptococcus terrestris
SEQUENCE: 10
FLFGWATAAQ Q                                                            11

SEQ ID NO: 11              moltype = AA   length = 15
FEATURE                    Location/Qualifiers
source                     1..15
                           mol_type = protein
                           note = Cryptococcus terrestris
                           organism = Cryptococcus terrestris
SEQUENCE: 11
QAYQIGIFAE PIYNT                                                        15

SEQ ID NO: 12              moltype = AA   length = 8
FEATURE                    Location/Qualifiers
source                     1..8
                           mol_type = protein
                           note = Cryptococcus terrestris
                           organism = Cryptococcus terrestris
SEQUENCE: 12
PSIWDWAS                                                                 8

SEQ ID NO: 13              moltype = AA   length = 10
FEATURE                    Location/Qualifiers
source                     1..10
                           mol_type = protein
                           note = Cryptococcus terrestris
                           organism = Cryptococcus terrestris
SEQUENCE: 13
EEPPFAYVPE                                                              10

SEQ ID NO: 14              moltype = DNA   length = 41
FEATURE                    Location/Qualifiers
misc_feature               1..41
                           note = 5'RACE GSP primer
source                     1..41
                           mol_type = other DNA
                           organism = synthetic construct
SEQUENCE: 14
gattacgcca agcttgcaaa gatcccgatc tggtacgcct g                           41

SEQ ID NO: 15              moltype = DNA   length = 39
FEATURE                    Location/Qualifiers
misc_feature               1..39
                           note = 3'RACE GSP primer
source                     1..39
                           mol_type = other DNA
                           organism = synthetic construct
SEQUENCE: 15
gattacgcca agcttttcct gtttggctgg gcgaccgcc                              39

SEQ ID NO: 16              moltype = DNA   length = 2942
FEATURE                    Location/Qualifiers
source                     1..2942
                           mol_type = genomic DNA
                           note = Cryptococcus terrestris
                           organism = Cryptococcus terrestris
SEQUENCE: 16
atgatcccgg caagtgcact ccttgccgcc gtacccctcc ttgcccaaca ggtgagcgcc        60
ggcatactgc gaagacagaa tgctgcgggt tcggattcgg cagcgcctga ctcgatcgcg       120
gatgcgtcca ccgtgtcgt ctcgtcgatc gccacgaag ccgtctcttc gggagcgaca        180
ggccttgtcg cgtccgtcgc catgtcattc gcctcgtcga tggcgactcc aacggccaca       240
gtgacgggcc taagctccga gacgggagcg ccttccaaca ccccaatgcc cagtgcctct       300
ggtagtgtcc ctacaaccac ctctgccgtc gggtctggcg acttcgactg ggtccagaca       360
gacggcctgc ccacgatcac gaccactttg gctactacga accaggacgc aatcactccg       420
acggcgacgg gccccgtcgg cggacagggc acccctgctg tcaacttcac cgactactct       480
tcatcgtcgc tcgagcagtt tttggaacgac tgggtaagtt aggccacggc tccatctgct       540
gacgagggtc caggagagct gacgcacagg tgggagaggt ggaggagccg ccgttcgcct       600
acgtcccgga accgcctaac ccgtaccgt taccgaacgc cccgcctcca atctacccg         660
agtactacac caagcgtccc aaggacattc tcccgacta caagttcccc aaagacttcc       720
tgtttggctg ggcgaccgcc gcgcagcagt gggaggggc cgtcaaggcg gatgggaagg       780
ggccgtccca ctgggactgg ccagccggt tcccggggtt cattgcggac aacacgactt       840
ccggtgagct gagaatgacc accttttcagt acgagagctc acttcagacg tcggagactt       900
```

```
gggatactat ttatacaaag agggttagcc ggggccgtat gagccagtgc tggatgctga    960
gtgcagacct cgctaggatc gctgcattgg gcgcaaacgt ttactctttc agcatgttct   1020
ggacacggat ctttcccttc ggcaaggccg actcgcctgt caatcaagcg ggcatcgact   1080
tctaccacga cttgatcgat tattcttgga gcctgggcat cgagcccgtc gtgtaagcct   1140
gtacagggggc ccatcttgaa ccccgctcat tacaggacat tgttccattg ggatacgccg   1200
ctcgccctcc agcttgagta cggaggtttc gccagcgagc gaatcattga tgactacgtc   1260
aactatgcgg tgagcagtac ggtcccttga gcacagcttg ggctgactcg taaggaaacc   1320
gtgttcaagg cgtacaacgg tagtgtgcac aaatgggtca cattcaacga gcctgtggtg   1380
ttctgcagcc aggtgagcaa ccaaagcgca tgttgagctg atcgaccaga tggcagcgcc   1440
cgtgaacgta agatgagcaa cgagccagac cagtgtcaat gctgaccatg accgtagact   1500
actctaccgc cgaacctcaa ctcgacaatc taccctata cctgcagcta tcacctcgtg   1560
ctagcccacg ccaagacggt caagcggttc agggagttga acattcgtga gctgatcggt   1620
accgcgtttc tggctgaaga cacgctgact gtcacagagg gccagatcgc tttcaagtcg   1680
gacaattttg tgtgagcatc gctgttgtgg ggagtcgtgc gtgctgaacc tttagcggta   1740
tcccgtggcg tgaggggaac caagaggaca tagatgcggt cgagcgccat caggtgaagt   1800
ctcgccagac cgcggaggct ccgaggctga ccggacaggc gtaccagatc gggatctttg   1860
ctgagccgat ctacaacacc ggagtgaggc ttccctccct cttccgcacg gtacacttgt   1920
ggcttatcga caggactggc ccgatatcgt gaagaatgat ctctccccccg acatccttcc   1980
tcgattcacg gatgacgaga tcgcgatgat caagtgcact gccgacttct tccccatcga   2040
tgtgagcctc caaacccacc cgtcgggaga cgggtcccga gtactacgcc taacgcacag   2100
ggctacaggg acgttatgt ccaggctgta ccgggggggtg tcgaagcttg cgtcgcgaac   2160
atcagcaacc cgctttggcc tgcttgcaac caagtcaagt gagactcgtc cagacccgc   2220
ctgtattgcg agcgccggca ctgacatgca gcttctgtac ggcccacagc accccgtcgc   2280
cgccgctgag ctgatgcata gatgattcca caccgccgg atgggcgatc ggcacgttcg   2340
gcaactggcc gacgacaccc tggctccaga acacctggca gtttgtgcgc cccttcctcg   2400
ctgatctggc aaagcggtac cccaccgaag gcggcatcta cctttcggaa tttggcttct   2460
ccgagccgtt cgaaaatgag tacgcctatc aactggctgc tgcaaggcat ggcgtactga   2520
gactcagtaa aaccttcatt taccagatca cccaggacag cggacggacg gcgtacttca   2580
acagttacct cggcgaagtg ttgaaaggta tcgttgaaga tggcattcct atcaagggcg   2640
tgttcggctg gagtatggtc gacaactttg aatggaactc tggcttgtct agtacgtcca   2700
cacggccgtg gatccttcga cgcccggtct gacccgtagc tcgcttcggc gtccaatacg   2760
ttgattacaa caggtgagct gtcgttttg ttttagggat cgcgatgctg atgcaaacag   2820
cccgacgcgt caacgaacgg tacgccgttc atgacctccc cctcgtccct gctgacgtcc   2880
agttcaagcg gtccgctctg gagatgagcg agttctggaa tgctcatcga tgttccgcct   2940
aa                                                                  2942
```

BETA-GALACTOSIDASE ENZYMES

TECHNICAL FIELD

The present invention relates to a novel β-galactosidase. For example, the β-galactosidase of the invention can be used in the production of galacto-oligosaccharides that are known as an intestinal bifidobacterium growth factor. The present application claims a priority date of Dec. 29, 2015 based on Japanese patent application No. 2015-257705, which is hereby incorporated by reference in its entirety.

SEQUENCE LISTING

The instant application contains a Sequence Listing which has been submitted in XML format and is hereby incorporated by reference in its entirety. The XML Sequence Listing file is named 17961625_SEQ.xml, was created on Jan. 5, 2023 and is 30,000 bytes in size.

BACKGROUND ART

Beta-galactosidase (EC3.2.1.23) is an enzyme that hydrolyzes the β-D-galactoside bond to release D-galactose, and, in general, it is widely distributed in microorganisms, and animals and plants. Beta-galactosidase is also referred to as lactase, and has been used as an enzyme for the production of a whey syrup from whey that is by-produced during the production of low-lactose milk for lactose intolerance or cheese, or as an active ingredient for medicines or supplements in patients with lactose intolerance. In addition, β-galactosidase has an ability to transfer galactose residue to form β-bond, and a method to prepare galacto-oligosaccharides (oligosaccharides with galactose residues) using this ability is known. Beta-galactosidases from a koji mold (*Aspergillus oryzae*), a yeast (*Sporobolomyces singularis, Kluyveromyces lacti, Cryptococcus laurentii*), and a bacterium (*Bacillus circulars, Sterigmatomyces elviae*) are known for use in these applications (see, for example, patent documents 1-3).

PRIOR ART DOCUMENTS

Patent Documents

Patent document 1: JP H3-216185 A
Patent document 1: JP H6-2057 B
Patent document 1: JP H7-236480 A

SUMMARY OF THE INVENTION

Problems to be Solved by the Invention

Many known β-galactosidase enzymes are unsuitable for industrial applications from viewpoints of heat resistance, pH stability, and others. Therefore, the present invention has a purpose of providing a novel β-galactosidase enzyme useful in industrial applications, particularly in the production of oligosaccharides, and applications thereof.

Means for Solving Problem

In order to achieve the above-described purpose, the present inventors have conducted screening of various kinds of microorganisms for such an above-mentioned enzyme. As a result, the present inventors were successful in finding a microorganism (wild-type strain) of the genus *Cryptococcus* which produces β-galactosidase that has high optimum temperature and superior heat resistance, and in addition, excellent transglycosylation activity. When the β-galactosidase enzyme produced by this strain was purified and extensively investigated for its properties, it turned out that as further superior properties, the enzyme is stable in an acidic pH range and the reaction of the enzyme with lactose as a substrate results in efficient production of linear oligosaccharides, which are considered to have particularly high utility as an intestinal bifidobacterium growth factor. This β-galactosidase enzyme is secreted outside the cell, which is advantageous also in terms of its production. Thus, as a result of extensive investigation, the present inventors have succeeded in obtaining a novel β-galactosidase enzyme (which is referred to as a "wild-type strain enzyme" for the purpose of description) that has an extremely high utility value as an enzyme for the production of oligosaccharides. The present inventors have also succeeded in determining the gene sequence of the wild-type strain enzyme. In addition, the present inventors have succeeded in the generation of useful mutant strains after repeating mutagenesis with UV treatment of the above-mentioned microorganism (wild-type strain), followed by screening, for example, in order to improve the productivity of the β-galactosidase enzyme. In an examination of properties of the resulting mutant strains, three β-galactosidase enzymes (mutant strain enzymes) from two mutant strains found. By further examination, the present inventors have succeeded in determining the amino acid sequences of these mutant strain enzymes. It has been found that each of these mutant enzymes is a fragment (portion) of the wild-type strain enzyme and does not exist in nature. More specifically, each of the resulting mutant strain enzymes is a mutated enzyme that has an amino acid sequence in which a part of the N-terminal amino acid sequence of the wild-type strain enzyme is deleted and that has improved stability (in terms of pH, temperature), compared with the wild-type strain enzyme.

The invention described below has been achieved based on the above-described results.

- [1] A β-galactosidase enzyme comprising the amino acid sequence of any one of SEQ ID NOs: 1 to 4 or an amino acid sequence that is 80% or more identical to said amino acid sequence.
- [2] The β-galactosidase enzyme according to [1], wherein the amino acid sequence is an amino acid sequence that is 85% or more identical to the amino acid sequence of any one of SEQ ID NOs: 1 to 4.
- [3] The β-galactosidase enzyme according to [1], wherein the amino acid sequence is an amino acid sequence that is 90% or more identical to the amino acid sequence of any one of SEQ ID NOs: 1 to 4.
- [4] The β-galactosidase enzyme according to any one of [1] to [3], wherein the amino acid sequence consists of an amino acid sequence having a length not exceeding that of the amino acid sequence of SEQ ID NO: 1.
- [5] A β-galactosidase enzyme which possesses the following enzymological properties:
  (1) an enzymatic action by which the enzyme has a lactose hydrolyzing activity and a transgalactosylation activity, wherein the activity of the enzyme to transfer a galactosyl residue via β-1,4-linkage is superior to that via β-1,6-, β-1,3-, or β-1,2-linkage;
  (2) an optimum temperature of 70° C.; and
  (3) a molecular weight of about 104 kDa, about 64 kDa, or about 61 kDa (by SDS-PAGE) for the enzyme without sugar chains.

[6] The β-galactosidase enzyme according to [5], which further possesses the following enzymological properties:
(4) an optimum pH of 4 to 5;
(5) a pH stability in which the enzyme is stable in a range of pH 2 to 8 (at 40° C. for 30 minutes); and
(6) a thermostability in which the enzyme is stable in a temperature range of 30° C. to 60° C. (at pH 6.0 for 30 minutes).

[7] The β-galactosidase enzyme according to [5], which further possesses the following enzymological properties:
(4) an optimum pH of 4 to 5;
(5) a pH stability in which the enzyme is stable in a range of pH 2 to 9 (at 40° C. for 30 minutes); and
(6) a thermostability in which the enzyme is stable in a temperature range of 30° C. to 65° C. (at pH 6.0 for 30 minutes).

[8] The β-galactosidase enzyme according to any one of [1] to [7], wherein the enzyme is derived from *Cryptococcus terrestris*.

[9] The β-galactosidase enzyme according to [8], wherein the *Cryptococcus terrestris* is *Cryptococcus terrestris* strain MM13-F2171 (Accession Number: NITE BP-02177) or APC-6431 (Accession Number: NITE BP-02178).

[10] An enzyme preparation comprising, as an active ingredient, the β-galactosidase enzyme according to any one of [1] to [9].

[11] A β-galactosidase gene consisting of a DNA selected from the group consisting of:
(a) a DNA encoding the amino acid sequences of any one of SEQ ID NOs: 1 to 4;
(b) a DNA consisting of the base sequence of any one of SEQ ID NOs: 5 to 8 and 16; and
(c) a DNA comprising a base sequence equivalent to that of any one of SEQ ID NOs: 5 to 8 and 16 and encoding a protein with β-galactosidase activity.

[12] A recombinant DNA comprising the β-galactosidase gene according to [11].

[13] A microorganism carrying the recombinant DNA according to [12].

[14] A method for producing a β-galactosidase enzyme, comprising the steps of:
(1) culturing cells of *Cryptococcus terrestris*; and
(2) collecting the β-galactosidase enzyme from the cultured medium and/or cells.

[15] The method according to [14], wherein the *Cryptococcus terrestris* is *Cryptococcus terrestris* strain MM13-F2171 or a mutant strain thereof.

[16] A method for producing a β-galactosidase enzyme, comprising the steps of:
(i) culturing the microorganism of [13] under conditions allowing the production of the protein encoded by the gene; and
(ii) collecting the protein that has been produced.

[17] A method for producing oligosaccharides, comprising a step of subjecting the β-galactosidase enzyme according to any one of [1] to [9] to a reaction with a disaccharide, oligosaccharide, or polysaccharide having at least one of β-1,3-, β-1,4-, and β-1,6-linkages.

[18] A method for producing oligosaccharides, comprising a step of subjecting the β-galactosidase enzyme according to any one of [1] to [9] to a reaction with lactose.

[19] The method according to or [18], wherein the reaction temperature in the step is from 30° C. to 75° C.

[20] An oligosaccharide mixture obtained by the method according to any one of [17] to [19].

[21] The oligosaccharide mixture according to [20], wherein 65% or more of the trisaccharides contained in the oligosaccharide mixture are composed of a linear oligosaccharide.

[22] Use of the β-galactosidase enzyme according to any one of [1] to [9] for the production of oligosaccharides.

BRIEF DESCRIPTION OF THE DRAWINGS

FIG. 6 represents a table showing the ability of a purified enzyme (wild-type strain enzyme) to produce oligosaccharides.

FIG. 7 represents tables showing that the ability of a purified enzyme (wild-type strain enzyme) to produce oligosaccharides. Lactose was used as a substrate and subjected to reactions with a purified enzyme derived from *Cryptococcus terrestris* strain MM13-F2171 (wild-type strain enzyme) and enzymes derived from the known β-galactosidase-producing strains. The degrees of polymerization of galacto-oligosaccharides (GOSs) when the production of GOSs reached a yield of about 50% were compared between the known β-galactosidase enzymes and the wild-type strain enzyme (upper table). The ratios of linear and branched oligosaccharides in the trisaccharides contained in the resulting oligosaccharide mixture were compared between the known β-galactosidase enzymes and the wild-type strain enzyme (lower table).

FIG. 9 represents a table showing the ability of a purified enzyme (mutant strain enzyme 3) to produce oligosaccharides.

FIG. 10 represents tables showing that the abilities of purified enzymes derived from mutant *Cryptococcus terrestris* strains (mutant strain enzymes) to produce oligosaccharides. Lactose was used as a substrate and subjected to reactions with purified enzymes derived from *Cryptococcus terrestris* strain M2 (mutant strain enzyme 1) and *Cryptococcus terrestris* strain M6 (mutant strain enzyme 3) and enzymes derived from the known β-galactosidase-producing strains. The degrees of polymerization of galacto-oligosaccharides (GOSs) when the production of GOSs reached a yield of about 50% were compared between the known β-galactosidase enzymes and the mutant strain enzymes (upper table). The ratios of linear and branched oligosaccharides in the trisaccharides contained in the resulting oligosaccharide mixture were compared between the known β-galactosidase enzymes and the mutant strain enzymes (lower table).

DETAILED DESCRIPTION OF THE INVENTION

1. Terminology

Figure 1:
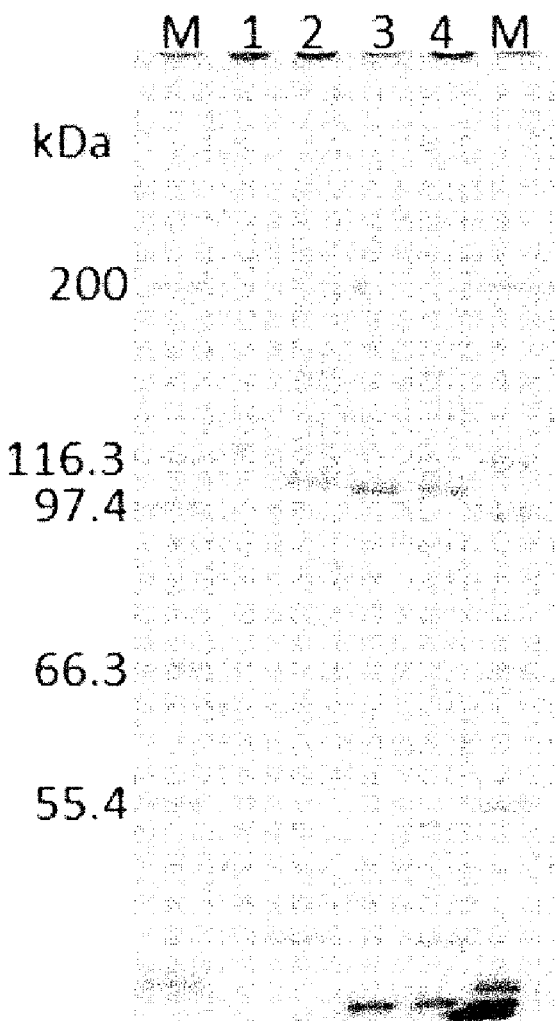
FIG. 1 shows a result of determination of the molecular weight (by SDS-PAGE) of a wild-type strain enzyme (β-galactosidase) derived from *Cryptococcus terrestris* strain MM13-F2171. M: molecular weight markers; Lane 1: no treatment; Lane 2: after treatment with O-glycosidase and neuraminidase; Lane 3: after treatment with PNGase F; Lane 4: after treatment with O-glycosidase, neuraminidase, and PNGase F. The molecular weights of the enzymes used for treatments for removal of sugar chains are 147 kDa for O-glycosidase, 43 kDa for neuraminidase, and 36 kDa for PNGase F.

The term "isolated" as used herein is used exchangeably with "purified." The term "isolated" is used to distinguish a material in a natural state, i.e., in a state in which it occurs in nature, from the material in a state in which it does not occur in nature. By a man-made operation of isolating a material of interest, the material will be in an "isolated state," which is a state different from its natural state. A material that has been isolated is clearly and determinately different from the material itself found in nature.

The purity of an isolated enzyme is not particularly limited. However, if an isolated enzyme is intended to be used for applications requiring that the enzyme be of high purity, then it is preferable that the isolated enzyme have a higher purity.

In general, β-galactosidase shows a lactose hydrolyzing activity (an activity to hydrolyze lactose by the action on the β-1,4 bond) and a transgalactosylation activity (an activity to transfer galactose). Therefore the "β-galactosidase activity" in the invention is intended to include such two activities. The lactose hydrolyzing activity can be measured by the lactose method described in Examples. The transgalactosylation activity can be evaluated by the method for measuring a degree of polymerization as to an ability to produce oligosaccharides as shown in Examples.

2. β-Galactosidase Enzymes and Producer Strains Therefor

A first aspect of the present invention is directed to providing a β-galactosidase enzyme and a producer strain therefor. As described above, the present inventors were successful in obtaining a β-galactosidase enzyme of high utility from a microorganism (wild-type strain) of the genus *Cryptococcus*, which is referred to as a "wild-type strain enzyme" for the purpose of description, and in addition, have determined its gene sequence. Furthermore, the present inventors have characterized three kinds of β-galactosidase produced by mutant strains derived from the *Cryptococcus* microorganism (mutant strain enzymes 1, 2, and 3), and determined their amino acid sequences. These three β-galactosidase enzymes were found to have a partial sequence of the full-length amino acid sequence of the wild-type strain enzyme (SEQ ID NO: 1), which is deduced from its gene sequence. Specifically, these mutant enzymes are one having an amino acid sequence in which the N-terminal 130 amino acid residues of the full-length amino acid sequence of the wild-type strain enzyme (SEQ ID NO: 1) are deleted, which is referred to as "mutant strain enzyme 1" for the purpose of description; one having an amino acid sequence in which the N-terminal 136 amino acid residues of the full-length amino acid sequence of the wild-type strain enzyme (SEQ ID NO: 1) are deleted, which is referred to as "mutant strain enzyme 2" for the purpose of description; and one having an amino acid sequence in which the N-terminal 141 amino acid residues of the full-length amino acid sequence of the wild-type strain enzyme (SEQ ID NO: 1) are deleted, which is referred to as "mutant strain enzyme 3" for the purpose of description. On the basis of these results and findings, a β-galactosidase enzyme of the present invention, which is also referred to hereinafter as an "present enzyme," has a feature of comprising the amino acid sequence of any one of SEQ ID NOs: 1 to 4 or an amino acid sequence equivalent to said amino acid sequence. The amino acid sequence of SEQ ID NO: 2 represents that of mutant strain enzyme 1; the amino acid sequence of SEQ ID NO: 3 represents that of mutant strain enzyme 2; and the amino acid sequence of SEQ ID NO: 4 represents that of mutant strain enzyme 3.

The term "equivalent amino acid sequence" in this case means an amino acid sequence which is partially different from the reference amino acid sequence (i.e. amino acid sequence of any one of SEQ ID NOs:1 to 4), but the difference does not substantially influence the function of the protein (β-galactosidase activity). Thus, tan enzyme having a polypeptide chain of the equivalent amino acid sequence shows a β-galactosidase activity. The degree of the activity is not particularly limited as long as the function of a β-galactosidase can be exhibited, but is preferably equivalent to or higher than that of the enzyme having a polypeptide chain of the reference sequence. Preferably, the length of the equivalent amino acid sequence is not longer than that of the sequence of SEQ ID NO: 1.

The term "partial difference in the amino acid sequence" typically means mutation (change) in the amino acid sequence caused by deletion or substitution of one to several (up to, for example, 3, 5, 7, or 10) amino acids composing the amino acid sequence, or addition, insertion, or combination thereof of one to several (up to, for example, 3, 5, 7, or 10) amino acids. The difference in the amino acid sequence is acceptable as long as the β-galactosidase activity is maintained (the activity may be varied to a degree). As long as the conditions are satisfied, the position of the difference in the amino acid sequence is not particularly limited, and the difference may arise in a plurality of positions. The term "plurality" means, for example, a number corresponding to less than about 20%, preferably less than about 15%, more preferably less than about 10%, even more preferably less than about 5% of the total amino acids, and most preferably less than about 1%. More specifically, the equivalent protein has, for example, about 80% or more, preferably about 85% or more, more preferably about 90% or more, much more preferably about 95% or more, even more preferably about 97% or more, and most preferably about 99% or more identity with the reference amino acid sequence. The difference of the amino acid sequence may arise in a plurality of positions.

Preferably, the equivalence protein is obtained by causing conservative amino acid substitution in an amino acid residue which is not essential for β-galactosidase activity. The term "conservative amino acid substitution" means the substitution of an amino acid residue with another amino acid residue having a side chain with similar properties. Amino acid residues are classified into several families according to their side chains, such as basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), nonpolar side chains (for example, alanine, valine, leucine, isoleucine, proline, phenylalanine, methionine, and tryptophan), β branched side chains (for example, threonine, valine, and isoleucine), and aromatic side chains (for example, tyrosine, phenylalanine, tryptophan, and histidine). Conservative amino acid substitution is preferably the substitution between amino acid residues in one family.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an equivalent nucleic acid sequence, for example, BLAST nucleotide search with score=100 and word length=12 may be carried out by the NBLAST program. In order to obtain an equivalent amino acid sequence, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see http://www.ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. The identity between two nucleic acid sequences can be determined by using the GAP program in the GCG software package (available at http://www.gcg-.com), with the gap weight of 50, and the gap length weight of 3.

The present enzyme may be a portion of a larger protein (for example, a fused protein). Examples of the sequence added to a fused protein include the sequences useful for purification of multiple histidine residues, and addition sequences which ensures stability in recombination production.

The present enzyme having the above-described amino acid sequence is readily prepared by a genetic engineering technique. For example, an appropriate host cell (for example, *Escherichia coli*) is transformed by a DNA encoding the present enzyme, and the protein expressed in the transformant is collected, and thereby preparing the present enzyme. The collected protein is treated as appropriate according to the intended use. The present enzyme thus obtained as a recombinant protein may be subjected to various modifications. For example, the present enzyme composed of a recombinant protein linked to any peptide or protein can be obtained by producing a recombinant protein using a vector into which a DNA encoding the present enzyme has been inserted together with other appropriate DNA. In addition, modification for causing addition of a sugar chain and/or a lipid, or N- or C-terminal processing may be carried out. These modifications allow, for example, extraction of a recombinant protein, simplification of purification, or addition of biological functions.

The present inventors were successful in characterizing enzymological properties of the novel β-galactosidase enzymes that had been successfully obtained (see the Examples section which follows). Thus, the present enzyme may be characterized by enzymological properties described below in (1) to (3).

(1) Enzymatic Action

The present enzyme has a lactose hydrolyzing activity and a transgalactosylation activity, wherein the activity of the enzyme to transfer a galactosyl residue via β-1,4-linkage is superior to that via β-1,6-, β-1,3-, or β-1,2-linkage. That is, the present enzyme has excellent activity to transfer a galactosyl residue via β-1,4-linkage. Therefore, the use of the inventive enzyme allows an efficient production of a product having the transferred sugar residue attached via β-1,4-linkage. For example, reaction of the present enzyme with lactose, which is a substrate for the enzyme, generates a mixture of trisaccharide oligosaccharides that is rich in linear oligosaccharides. A linear oligosaccharide is an oligosaccharide having a structure in which the constituent monosaccharides are connected by β-1,4-glycosidic linkage, in contrast to a branched oligosaccharide which contains other linkages (e.g. β-1,6-glycosidic linkage, β-1,2-glycosidic linkage) in addition to β-1,4-glycosidic linkage. In cases of trisaccharide oligosaccharides obtained when lactose is used as a substrate for reaction with the present enzyme under reaction conditions described in the Examples section which follows (in the subsection titled "Examination on oligosaccharide production ability 1"), 65% or more, preferably 70% or more, further preferably 72% or more, still further preferably 73% or more, more preferably 75% or more, of the resulting trisaccharide oligosaccharides are composed of a linear oligosaccharide (O-β-D-galactopyranosyl-(1→4)-O-β-D-galactopyranosyl-(1→4)-D-glucose).

In these cases, the linear oligosaccharide produced by the inventive enzyme is a galacto-oligosaccharide. In general, the galacto-oligosaccharide is represented by Gal-(Gal)n-Glc, wherein n is 0 to 5 or so, and Gal is a galactose residue and Glc is a glucose residue. The type of linkage between sugar residues includes β-1,4, β-1,6, β-1,3, and β-1,2, and besides these, α-1,3, α-1,6, and others. In the present invention, it is intended that lactose does not correspond to a galacto-oligosaccharide. Therefore, a "galacto-oligosaccharide (GOS)" as used herein means a galacto-oligosaccharide of two or more sugar residues, i.e., having a degree of polymerization of 2 or more, excluding lactose.

The present enzyme is superior in transglycosylation activity. When lactose is used as a substrate for reaction with the present enzyme under reaction conditions described in the Examples section which follows (in the subsection titled "Examination on oligosaccharide production ability 1"), the resulting galacto-oligosaccharides will account for 45% or more of the total sugar amount after the reaction, with varying depending on the reaction temperature condition (and 50% or more when the reaction has been carried out around the optimum temperature).

(2) Optimum Temperature

The present enzyme has an optimum temperature of 70° C. Such a high optimum temperature of the inventive enzyme is advantageous for use as an enzyme for the production of oligosaccharides. When the present enzyme is used for the production of oligosaccharides, the process (reaction) temperature can be set to be higher. Increased process temperatures result in an increase in the solubility of the substrate for the reaction, allowing it to be charged at higher concentrations. As a result, an increase in the amount (yield) of galacto-oligosaccharides produced per reaction volume can be expected. The reduction of costs for constration can also be achieved. Furthermore, it is possible to reduce the risk of contamination. Herein, the optimum temperature can be determined by a method in which measurements are made using acetate buffer (pH 6.0) and with lactose as a substrate.

(3) Molecular Weight

The wild-type strain enzyme and mutant strain enzymes 1 to 3 that are encompassed by the inventive enzyme each comprise a sugar chain(s); when the molecular weights of these enzymes were determined by SDS-PAGE after removal of N- and O-linked sugar chains, they were found to have a molecular weight of 104 kDa (for the wild-type strain enzyme), 64 kDa (for mutant strain enzyme 1), 61 kDa (for mutant strain enzyme 2), and 61 kDa (for mutant strain enzyme 3). On the basis of these findings, according to one embodiment of the present enzyme, the inventive enzyme without sugar chains has a molecular weight of 104 kDa (by SDS-PAGE). According to another embodiment of the present enzyme, the inventive enzyme without sugar chains has a molecular weight of 64 kDa (by SDS-PAGE). According to further another embodiment of the present enzyme, the inventive enzyme without sugar chains has a molecular weight of 61 kDa (by SDS-PAGE). The above-mentioned enzymes when not subjected to treatments for removing sugar chains were found to have a molecular weight of 120 kDa (for the wild-type strain enzyme), 71 kDa (for mutant strain enzyme 1), 66 kDa (for mutant strain enzyme 2), and 66 kDa (for mutant strain enzyme 3).

The present enzyme may be further characterized by enzymological properties described below in (4) to (6).

(4) Optimum pH

The present enzyme has an optimum pH of 4 to 5. The optimum pH is determined, for example, on the basis of the results from measurements made using 0.1 M glycine buffer in the pH range of pH 2 to 3, 0.1 M citrate buffer in the pH range of pH 3 to 6, 0.1 M acetate buffer in the pH range of pH 5 to 6, 0.1 M phosphate buffer in the pH range of pH 7 to 8, and 0.1 M sodium carbonate buffer in the pH range of pH 9 to 10.

(5) pH Stability

In one embodiment, the present enzyme exhibits stable enzymatic activity in the pH range of pH 2 to 8, and in another embodiment, in the pH range of pH 2 to 9. In other words, if the pH of an enzyme solution to be subjected to treatments is within this pH range, then the enzyme after pH treatments at 40° C. for 30 minutes shows an activity of 80% or more of the maximal activity. The pH stability is determined, for example, on the basis of the results from measurements made using 0.1 M glycine buffer in the pH range of pH 2 to 3, 0.1 M citrate buffer in the pH range of pH 3 to 6, 0.1 M acetate buffer in the pH range of pH 5 to 6, 0.1 M phosphate buffer in the pH range of pH 7 to 8, and 0.1 M sodium carbonate buffer in the pH range of pH 9 to 10.

(6) Thermostability

In one embodiment, the present enzyme retains an activity of 80% or more of the maximal activity, even when the enzyme is treated for 30 minutes in acetate buffer (pH 6.0) under temperature conditions of 30° C. to 60° C. In another embodiment, the present enzyme retains an activity of 80% or more of the activity, even when the enzyme is treated for 30 minutes in acetate buffer (pH 6.0) under temperature conditions of 30° C. to 65° C.

The present enzyme preferably is β-galactosidase derived from *Cryptococcus terrestris*. Here, by "β-galactosidase derived from *Cryptococcus terrestris*" is meant a β-galactosidase enzyme produced by a microorganism (of either a wild-type strain or a mutant strain) which is classified into *Cryptococcus terrestris*, or a β-galactosidase enzyme obtained by genetic engineering procedures using the β-galactosidase gene from a microorganism (of either a wild-type strain or a mutant strain) which is classified into *Cryptococcus terrestris*. Therefore, "β-galactosidase derived from *Cryptococcus terrestris*" encompasses a recombinant enzyme that is produced by a host microorganism into which the β-galactosidase gene (or a modified gene thereof) obtained from *Cryptococcus terrestris* has been introduced.

A strain of *Cryptococcus terrestris* from which the present enzyme is derived is referred to as a producer strain for the inventive enzyme, for the purpose of description.

As demonstrated in the Examples section which follows, the present inventors were successful in isolating and purifying β-galactosidase enzymes having the above-described properties, from *Cryptococcus terrestris* strain MM13-F2171 and its mutant strains M2 and M6. *Cryptococcus terrestris* strains MM13-F2171 and M2 have been deposited at a depository, as described below, and are readily available.

*Cryptococcus terrestris* Strain MM13-F2171
  Depository: Patent Microorganisms Depositary, National Institute of Technology and Evaluation (Room 122, 2-5-8 Kazusa Kamatari, Kisarazu-shi, Chiba, 292-0818, JAPAN)
  Identification reference: *Cryptococcus terrestris* MM13-F2171
  Date of deposit: Dec. 10, 2015
  Accession number: NITE BP-02177

*Cryptococcus terrestris* Strain M2
  Depository: Patent Microorganisms Depositary, National Institute of Technology and Evaluation (Room 122, 2-5-8 Kazusa Kamatari, Kisarazu-shi, Chiba, 292-0818, JAPAN)
  Identification reference: *Cryptococcus terrestris* APC-6431
  Date of deposit: Dec. 10, 2015
  Accession number: NITE BP-02178

3. Gene Encoding β-Galactosidase, Recombinant DNA, and Transformant

The second aspect of the invention relates to a gene encoding the present enzyme. In one embodiment, the gene of the invention includes a DNA that encodes an amino acid sequence of any one of SEQ ID NOs: 1 to 4. Specific examples of the embodiment are the cDNA consisting of the base sequence of SEQ ID NO: 5 (encoding the amino acid sequence of SEQ ID NO: 1), the cDNA consisting of the base sequence of SEQ ID NO: 6 (encoding the amino acid sequence of SEQ ID NO: 2), the cDNA consisting of the base sequence of SEQ ID NO: 7 (encoding the aminoacid sequence of SEQ ID NO: 3), and the cDNA consisting of the base sequence of SEQ ID NO: 8 (encoding the amino acid sequence of SEQ ID NO: 4). Further example is the genome DNA consisting of SEQ ID NO: 16. This genome DNA corresponds to the cDNA of SEQ ID NO: 5.

The gene encoding the present enzyme is typically used in preparation of the present enzyme. According to a genetic engineering procedure using the gene encoding the present enzyme, the present enzyme in a more homogeneous state can be obtained. Further, the method can be a preferable method also in the case of preparing a large amount of the present enzyme. Note that uses of the gene encoding the present enzyme are not limited to preparation of the present enzyme. For example, the nucleic acid can also be used as a tool for an experiment intended for clarification of action mechanisms of the present enzyme or a tool for designing or preparing a mutant (modified form) of the present enzyme.

The "gene encoding the present enzyme" herein refers to a nucleic acid capable of obtaining the present enzyme when it is expressed, and includes, as a matter of course of a nucleic acid having a base sequence corresponding to the amino acid sequence of the present enzyme, also a nucleic acid obtained by adding a sequence that does not code for an amino acid sequence to such a nucleic acid. Degeneracy of a codon is also considered.

The gene of the present invention can be prepared in an isolated state by using a standard genetic engineering technique, a molecular biological technique, a biochemical technique, a chemical synthesis, a PCR method (e.g. an overlap extension PCR) or a combination thereof, with reference to sequence information disclosed in the present specification or attached sequence list.

In general, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Thus, as another embodiment, the present invention provides DNA encoding a protein having a base sequence equivalent to the reference base sequence (i.e., any one of SEQ ID NO: 5 to 8, 16) and having the β-galactosidase activity (hereinafter, which is also referred to as "equivalent DNA"). The "equivalent base sequence" herein denotes a base sequence which is partly different from the reference base sequence but in which the function (herein, β-galactosidase activity) of the protein encoded by the sequence is not substantially affected by the difference.

A specific example of the equivalent DNA includes DNA that hybridizes to the complementary base sequence of the reference base sequence under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15 M NaCl, 15 mM sodium citrate, pH 7.0), 5×Denhardt solution, 1% SDS, 10% dextran sulfate, 10 μg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution 50% formamide, 5×SSC (0.15 M NaCl, 15 mM sodium citrate, pH 7.0), 1×Denhardt solution, 1% SDS, 10% dextran sulfate, 10 μg/ml denatured salmon sperm DNA, and 50 mM phosphate buffer (pH 7.5)) is used.

Another specific example of the equivalent DNA can include DNA encoding a protein having a base sequence which includes substitution, deletion, insertion, addition or inversion in one or a plurality of bases (preferably one to several bases) in the reference base sequence, and which has a β-galactosidase activity. The substitution, deletion, or the like, of the base may occur in a plurality of sites. The "plurality" herein denotes, for example, 2 to 40 bases, preferably 2 to 20 bases, and more preferably 2 to 10 bases, although it depends upon the positions or types of the amino acid residue in the three-dimensional structure of the protein encoded by the DNA. The equivalent DNA shows a 60% or more identity for example, preferably a 70% or more identity, more preferably a 80% or more identity, more and more preferably a 85% or more identity, much more preferably a 90% or more identity, even more preferably 95% or more identity, and most preferably a 99% or more identity with the reference base sequence. The above-mentioned equivalent DNA can be obtained by modifying the reference DNA so as to include substitution, deletion, insertion, addition and/or inversion of base by using treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultraviolet ray. A further example of the equivalent DNA can include DNA having difference in base as mentioned above due to polymorphism represented by SNP (single nucleotide polymorphism).

Another embodiment of the present invention relates to a nucleic acid having the complementary base sequence to the base sequence of the gene encoding the present enzyme. Another embodiment of the present invention provides a nucleic acid having a base sequence with an identity of at least about 60%, 70%, 80%, 85%, 90%, 95%, 98%, 99%, or 99.9% to the base sequence of the gene encoding the present enzyme or the complementary base sequence thereto.

Another aspect of the present invention relates to a recombinant DNA containing the gene of the present invention (the gene encoding the present enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of DNA into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

The present invention further relates to a transformant into which the recombinant DNA, which contains the gene of the present invention, of the present invention is introduced. In the transformant of the preset invention, the gene of the present invention exists as an exogenous molecule. Preferably, the transformant of the present invention can be preferably prepared by transfection or transformation using the vector of the present invention mentioned above. The transfection and transformation can be carried out by, for example, a calcium phosphate coprecipitation method, electroporation (Potter, H. et al., Proc. Natl. Acad. Sci. U.S.A. 81, 7161-7165(1984)), lipofection (Felgner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), a method by Hanahan (Hanahan, D., J. Mol. Biol. 166, 557-580 (1983)), a lithium acetate method (Schiestl, R. H. et al., Curr. Genet. 16, 339-346 (1989)), protoplast-polyethylene glycol method (Yelton, M. M. et al., Proc. Natl. Acad. Sci. 81, 1470-1474 (1984)), and the like.

The host cell is not particularly limited as long as the present enzyme can be expressed, and it can be selected from, for example, *Bacillus* genus bacteria (e.g. *Bacillus subtillis*, *Bacillus licheniformis*, *Bacillus circulans*, etc.), lactic acid bacteria (e.g. *Lactococcus*, *Lactobacillus*, *Streptococcus*, *Leuconostoc*, *Bifidobacterium*, etc.), other bacteria (e.g. *Escherichia*, *Streptomyces*, etc.), yeast (e.g. *Saccharomyces*, *Kluyveromyces*, *Candida*, *Torula*, *Torulopsis*, *Pichia*, *Schizosaccharomyces*, etc.), and filamentous fungi (*Eumycetes*) (e.g. *Aspergillus* genus fungi such as *Aspergillus oryzae* and *Aspergillus niger*, *Penicillium* genus fungi, *Trichoderma* genus fungi, *Fusarium* genus fungi, etc.).

4. Methods for Production of β-Galactosidase Enzymes

A second aspect of the present invention is directed to providing a method for producing a β-galactosidase enzyme. In one embodiment of the method of the present invention, the following steps are carried out: a step of culturing cells of *Cryptococcus terrestris* (step (1)); and a step of collecting the β-galactosidase enzyme from the cultured medium and/or cells (step (2)). Preferably, as the *Cryptococcus terrestris*, use is made of *Cryptococcus terrestris* strain MM13-F2171 or a mutant strain thereof, for example, *Cryptococcus terrestris* APC-6431 (strain M2) and further mutant strains thereof. Conditions and methods for culturing cells of *Cryptococcus terrestris* are not particularly limited, as long as the inventive enzyme is produced. Thus, methods and culture conditions that are suitable for culturing a microorganism to be used can be set as appropriate, with the proviso that the inventive enzyme is produced. Although the culturing may be by either liquid culture or solid culture, liquid culture is preferably employed. Taking liquid culture as an example, culturing conditions therefor will be described below.

As the medium, any medium can be used as long as microorganisms to be used can grow. For example, a medium supplemented with a carbon source such as glucose, sucrose, gentiobiose, soluble starch, glycerin, dextrin, molasses, and organic acid; and further, a nitrogen source such as ammonium sulfate, ammonium carbonate, ammonium phosphate, ammonium acetate, or peptone, yeast extract, corn steep liquor, casein hydrolysate, bran, and meat extract; and furthermore, an inorganic salt such as potassium salt, magnesium salt, sodium salt, phosphate salt, manganese salt, iron salt, and zinc salt, and the like, can be used. In order to promote the growth of transformants to be used, vitamin, amino acid, and the like, may be added to the medium. The medium is cultured under the aerobic conditions such that the pH of the medium is adjusted to, for example, about 3 to 8 (preferably about 4 to 7), and the culture temperature is generally about 20° C. to 40° C. (preferably about 25° C. to 35° C.) for 1 to 10 days (preferably 3 to 6 days). An example of the culture method may include a shake culture method, and an aerobic submerged culture method by using a jar fermenter.

After culturing under the above conditions, the target protein is collected from the culture solution or the cell bodies (step (2)). When it is collected from the culture solution, the present enzyme can be obtained by separation and purification by removing insoluble matters by, for example, filtration of culture supernatant, centrifugation, and the like, followed by carrying out, for example, concentration by ultrafiltration membrane, salting out by ammonium sulfate precipitation, dialysis, various types of chromatography of an ion-exchange resin or an appropriate combination thereof. On the other hand, when it is collected from cell bodies, the target protein can be obtained by pulverizing the cell bodies by pressuring treatment, ultrasonic treatment, or the like, followed by separation and purification thereof similar to the above. After collection of the cell bodies from a culture solution by filtration, centrifugation, etc., a series of processes (pulverizing, separation, and purification of cell bodies) mentioned above may be carried out.

In another embodiment of the present invention, the β-galactosidase is produced by using the above-mentioned transformant. In the production method in this embodiment, the transformant is cultured under the conditions such that a protein encoded by a gene introduced therein is produced (step (i)). The culture conditions of transformant are known as to various vector-host systems, and a person skilled in the art can easily set an appropriate culture condition. Following to the culturing step, the produced protein (β-galactosidase) is collected (step (ii)). Collection and following purification can be conducted in the same manner as the above embodiment.

The purification degree of β-galactosidase is not particularly limited. Furthermore, the final form of the β-galactosidase may be a liquid state or a solid state (including a powdery state).

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

5. Enzyme Preparation

The present enzyme is provided, for example, in the form of an enzyme preparation. The enzyme preparation may contain an excipient, a buffer agent, a suspending agent, a stabilizer, a preservative, an antiseptic, saline and the like besides the active ingredient (i.e. the present enzyme). The degree of purity of the present enzyme is not particularly limited. Thus, the present enzyme may be a crude or purified enzyme. As the excipient, lactose, sorbitol, D-mannitol, maltodextrin, white soft sugar, common salt and the like can be used. As the buffer agent, phosphates, citrates, acetates and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, benzalkonium chloride, paraoxybenzoic acid, chlorobutanol and the like can be used.

6. Uses of β-Galactosidase Enzymes

A further aspect of the present invention is directed to providing uses of the present enzyme and enzyme preparation. Examples of such uses include production of galacto-oligosaccharides, production of low-lactose milk, and production of medicines or supplements for patients with lactose intolerance. The galacto-oligosaccharides produced by the present invention are used, for example, as an intestinal bifidobacterium growth factor. The present enzyme or enzyme preparation is particularly useful in the production of galacto-oligosaccharides. The use of the present enzyme or enzyme preparation makes it possible that lactose is used as a raw material to produce a mixture of galacto-oligosaccharides, which is rich in linear oligosaccharides, i.e., has a high ratio of linear oligosaccharides relative to branched oligosaccharides. In producing galacto-oligosaccharides, for example, 75 U to 5000 U of the present enzyme is added to one liter of a preheated solution containing 30% to 65% lactose (pH 5.0) and the mixture is allowed to react at 30° C. to 75° C. for 15 to 50 hours, thereby to result in the generation of galacto-oligosaccharides. Since the inventive enzyme has a high optimum temperature, the process (reaction) temperature can be set to be a higher temperature (for example, 40° C. to 75° C., preferably 50° C. to 75° C., further preferably 60° C. to 75° C., still further preferably 65° C. to 75° C.). Increased process temperatures result in an increase in the solubility of the substrate for the reaction, allowing it to be charged at higher concentrations. The raw material (substrate) in the production of oligosaccharides using the present enzyme or enzyme preparation is preferably lactose, but is not limited thereto. It is possible to employ, as raw material, a disaccharide, oligosaccharide, or polysaccharide having at least one of β-1,3-, β-1,4- and β-1,6-linkages.

EXAMPLES

1. Obtainment of Novel β-Galactosidase Enzymes

In order to obtain a β-galactosidase enzyme suitable for the production of galacto-oligosaccharides, various kinds of microorganisms were screened. As a result, it turned out that a microorganism of *Cryptococcus terrestris* contained in a soil sample that had been collected near Heho Airport in Myanmar in October 2013 under a "Joint Project for the Conservation and Sustainable Use of Biological Genetic Resources in an Asian Area" with the National Institute of Technology and Evaluation was a promising producer strain for β-galactosidase. An attempt was made to purify β-galactosidase from this microbial strain (*Cryptococcus terrestris* strain MM13-F2171). *Cryptococcus terrestris* strain MM13-F2171 was deposited on Dec. 10, 2015 at the Patent Microorganisms Depositary, National Institute of Technology and Evaluation, under the name of *Cryptococcus terrestris* MM13-F2171, to which the Accession Number NITE BP-02177 was assigned.

(1) Method for Measuring Lactose Hydrolyzing Activity

Five milliliters (5.0 mL) of 0.1 M acetate buffer (pH 6.0) containing 12% lactose is preheated at 40° C. for 10 minutes. To this solution is added 1 mL of a sample, and the mixture is left stand at 40° C. for 10 minutes, followed by addition of 1.0 mL of 1.5 M sodium hydroxide. The reaction mixture is further left stand at 40° C. for 5 minutes, thereby to stop the reaction. The reaction solution was cooled in an ice-water bath, and then neutralized by addition of 1.0 mL of 1.5 M hydrochloric acid. For a 100 µl aliquot of this reaction solution, the amount of glucose in the reaction solution was determined using a glucostat method (a glucose kit, Glucose CII-Test Wako, from Wako Pure Chemical Industries, Ltd.). The amount of the enzyme producing 1 µmol glucose per minute was defined as one unit (1 U).

(2) Purification Procedures and Results

*Cryptococcus terrestris* strain MM13-F2171 was cultured in a liquid medium (2.0% lactose, 2.0% Yeast Extract, 0.1% $KH_2PO_4$, 0.05% $MgSO_4 \cdot 7H_2O$, pH 5.0) at 30° C. for 4 days with shaking (at 200 revolutions per minute). After the culturing was completed, about 3 L supernatant was collected by centrifugation, and then subjected to concentration and desalting treatment with an ultra-filtration membrane (AIP-1013D with a membrane inner size of 0.8 mm; Asahi Kasei Chemicals Corp.). In the desalting treatment, 20 mM acetate buffer (pH 6.0) was used.

The concentrated solution was loaded onto an anion-exchange column HiTrap DEAE FF (GE Healthcare Biosciences), which had been equilibrated with 20 mM acetate buffer (pH 6.0). Absorbed fractions were eluted with a gradient using 20 mM acetate buffer (pH 6.0) containing 1 M NaCl, and measured for enzyme activity.

Fractions with enzyme activity were pooled, and then subjected to dialysis against 20 mM acetate buffer (pH 6.0) containing 1.8 M ammonium sulfate.

The enzyme-active fraction obtained after the dialysis was loaded onto a hydrophobic column HiTrap Phenyl HP (GE Healthcare Biosciences), which had been equilibrated with 20 mM acetate buffer (pH 6.0) containing 1.8 M ammonium sulfate. Absorbed fractions were eluted with a gradient using 20 mM acetate buffer (pH 6.0), and measured for enzyme activity. Fractions with enzyme activity were pooled, and then subjected to dialysis against 20 mM acetate buffer (pH 6.0) containing 0.2 M NaCl.

The enzyme-active fraction obtained after the dialysis was loaded onto a gel filtration column HiLoad Superdex 200 prep grade (GE Healthcare Biosciences), which had been equilibrated with 20 mM acetate buffer (pH 6.0) containing 0.2 M NaCl, and then fractions with enzyme activity were collected. The enzyme had a molecular weight of about 266 kDa when determined by a gel filtration method using this HiLoad Superdex 200 prep grade column. When this result is considered in combination with the results of SDS-PAGE analysis (see below), it is supposed that the enzyme is in the form of a dimer.

Subsequently, the molecular weight of the purified wild-type strain enzyme was determined by SDS-PAGE. First, samples of the purified wild-type strain enzyme were subjected to denaturation (in a denaturing buffer in a boiling water bath for 10 minutes), followed by treatments for removal of O-linked sugar chains (using both O-glycosidase and neuraminidase; O-Glycosidase & Neuraminidase Bundle, New England Biolabs) and/or N-linked sugar chains (using PNGase F; New England Biolabs). The conditions for these enzyme treatments followed the protocols provided with the respective enzymes. After the treatments, the molecular weights of the resulting products were determined by SDS-PAGE. The results of SDS-PAGE are shown in FIG. 1. The wild-type strain enzyme was found to have a molecular weight of 120 kDa after no treatment (lane 1), 106 kDa after removal of O-linked sugar chains (lane 2), 104 kDa after removal of N-linked sugar chains (lane 3), and 104 kDa after removal of both O-linked and N-linked sugar chains (lane 4).

2. Internal Amino Acid Sequences of the Purified Enzyme

The results of analysis of the amino acid sequence of the purified enzyme revealed that the enzyme comprises the following amino acid sequences:

```
                                          (SEQ ID NO: 9)
GVQYVDYNSPT (SEQ ID NO: 10)
FLFGWATAAQQ (SEQ ID NO: 11)
QAYQIGIFAEPIYNT (SEQ ID NO: 12)
PSIWDWAS,
and (SEQ ID NO: 13)
EEPPFAYVPE.
```

3. Determination of the Gene Sequence of the Wild-Type Strain Enzyme

An attempt was made to determine the gene sequence encoding the β-galactosidase produced by *Cryptococcus terrestris* strain MM13-F2171. *Cryptococcus terrestris* strain MM13-F2171 was cultured in a liquid medium (2.0% lactose, 2.0% Yeast Extract, 0.1% $KH_2PO_4$, 0.05% $MgSO_4.7H_2O$, pH 5.0) at 30° C. for 24 hours with shaking (at 200 revolutions per minute). After the culturing was completed, cells were harvested. Total RNA was prepared in accordance with the protocol of the RNeasy Mini Kit (QIAGEN) for RNA extraction from yeast cells (mechanical disruption of cells). The synthesis of cDNAs from the resulting total RNA was performed using the SMARTer RACE 5'/3' kit (TaKaRa), and then 5' and 3' RACE PCR reactions were carried out. The 5'RACE GSP primer used had the sequence GATTACGCCAAGCTTgcaaagatccc-gatctggtacgcctg (SEQ ID NO: 14), and the 3'RACE GSP primer used had the sequence GATTACGC-CAAGCTTttcctgtttggctgggcgaccgcc (SEQ ID NO: 15). The base sequences of the resulting RACE PCR products were analyzed to determine the full-length cDNA sequence (SEQ ID NO: 5). The putative amino acid sequence encoded by the full-length cDNA sequence is of SEQ ID NO: 1.

By further investigation, the genomic DNA sequence encoding the β-galactosidase produced by *Cryptococcus terrestris* strain MM13-F2171 (SEQ ID NO: 16) was successfully determined.

Figure 2:
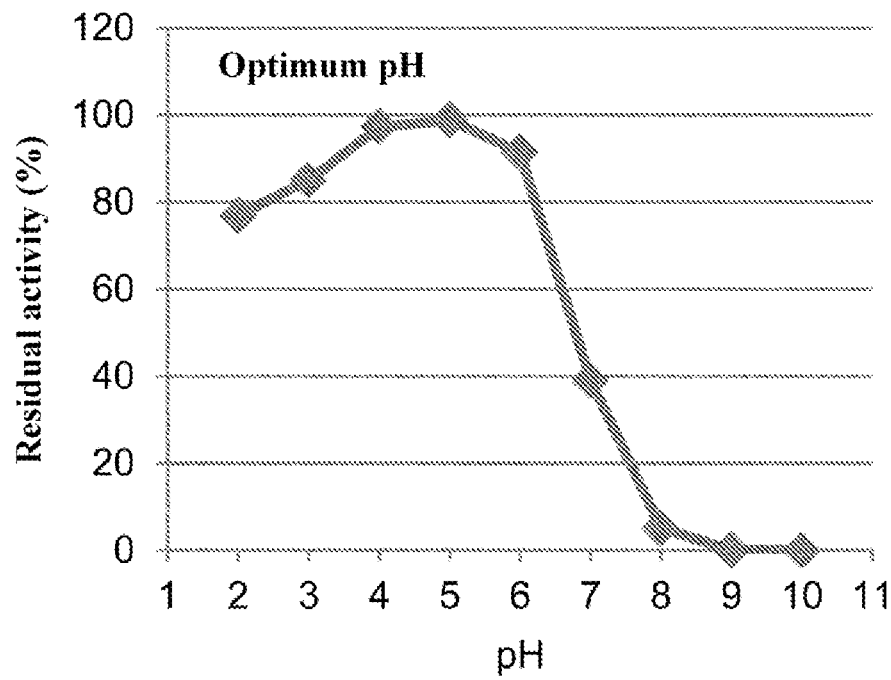
FIG. 2 is a graph showing the optimum pH of a purified enzyme.

4. Examination of Properties of the Purified Enzyme (1) Optimum pH and pH Stability The optimum pH and pH stability of the purified enzyme were examined using a lactose hydrolyzing activity as an indicator. Examinations for optimum pH were performed using 0.1 M glycine buffer in the pH range of pH 2 to 3, 0.1 M citrate buffer in the pH range of pH 3 to 6, 0.1 M acetate buffer in the pH range of pH 5 to 6, 0.1 M phosphate buffer in the pH range of pH 7 to 8, and 0.1 M sodium carbonate buffer in the pH range of pH 9 to 10. The results from enzyme activity measurements at different pHs are shown in FIG. 2. The purified enzyme was found to have an optimum pH of 4 to 5.

Figure 3:
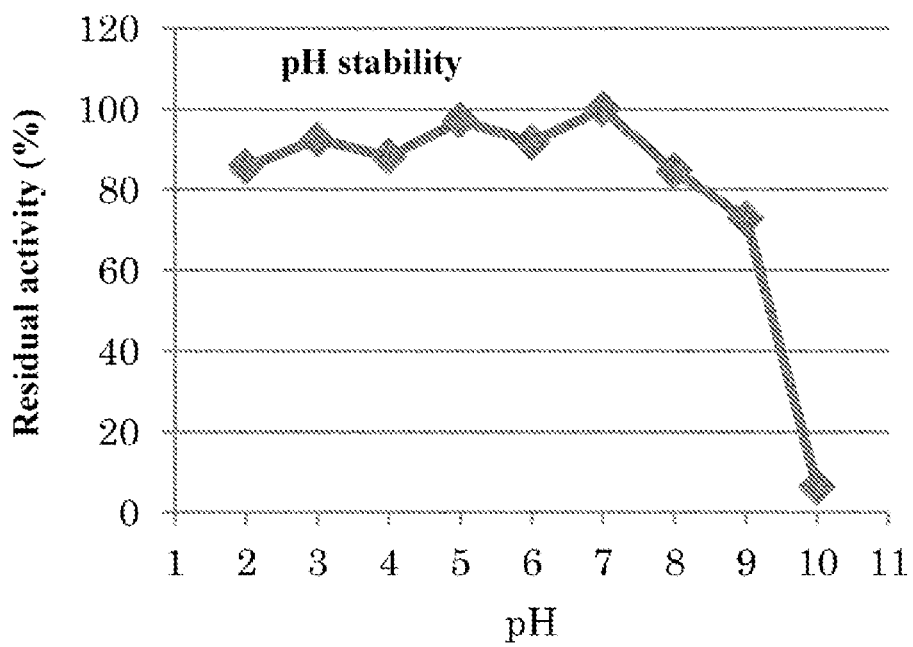
FIG. 3 is a graph showing the pH stability of a purified enzyme.

The pH stability of the purified enzyme was examined by heating it at 40° C. for 30 minutes in buffers of different pHs (using the above-described buffers) and then measuring the residual enzyme activity. The results from residual enzyme activity measurements at different pHs are shown in FIG. 3. The purified enzyme exhibited stable enzyme activity in the pH range of pH 2 to 8.

(2) Optimum Temperature and Thermostability

Figure 4:
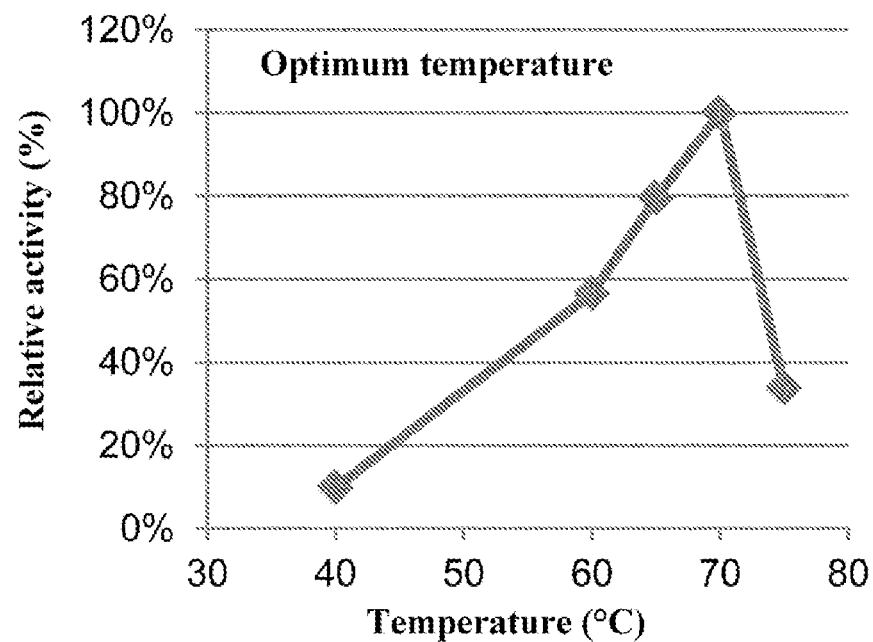
FIG. 4 is a graph showing the optimum temperature of a purified enzyme.
Figure 5:
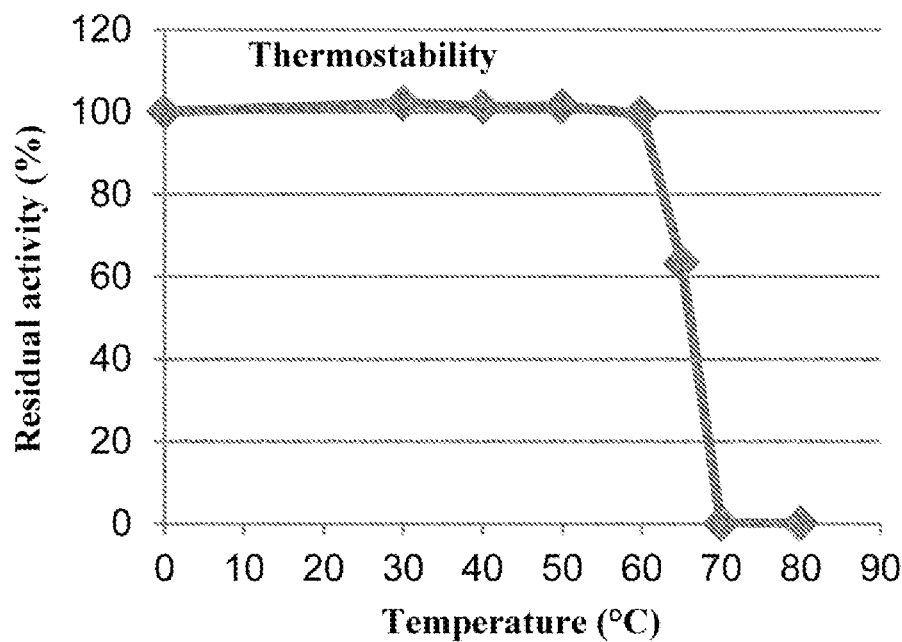
FIG. 5 is a graph showing the thermostability of a purified enzyme.

To examine the optimum temperature of the purified enzyme, acetate buffer (pH 6.0) was used and the lactose hydrolyzing activity was measured at different temperatures. The results from enzyme activity measurements at different temperatures are shown in FIG. 4. The purified enzyme was found to have an optimum temperature of 70° C. To examine the thermostability of the purified enzyme, the lactose hydrolyzing activity was measured after the enzyme was heated in acetate buffer (pH 6.0) for 30 minutes at different temperatures. The results from enzyme activity measurements at different temperatures are shown in FIG. 5. It was found that the purified enzyme was stable between 30° C. and 60° C. and the enzyme activity was retained at levels of 80% or more of the activity.

5. Examination on Oligosaccharide Production Ability 1

(1) Methods

The purified enzyme was examined for the ability to produce oligosaccharides. One unit (1 U) of the purified wild-type strain enzyme per 1 g of lactose was added to aliquots of a 53% lactose solution that had been preheated to specified reaction temperatures, which then were subjected to reaction at those temperatures for 24 hours. The reaction solutions after the reaction was completed were analyzed by HPLC (under the conditions described below) to determine the composition of sugars contained therein. The results from determination of the composition of sugars allow an evaluation of the transglycosylation activity.

Examinations were made for the degrees of polymerization of galacto-oligosaccharides (GOSs) and of branching of trisaccharides when the production of galacto-oligosaccharides by the purified enzyme (wild-type strain enzyme) reached a yield of about 50%. Reactions were carried out in accordance with the above-described procedures, and at 65° C. for 24 hours as conditions where the production of GOSs by the purified enzyme (derived from *Cryptococcus terrestris*) reached a yield of about 50%. For comparison, the ability to produce oligosaccharides was also measured for other β-galactosidase enzymes from known β-galactosidase producing strains *Cryptococcus laurentii* (described in JP H6-2057 B) and *Sporobolomyces singularis* (described in JP H3-216185 A). The enzymes derived from *Cryptococcus laurentii* and *Sporobolomyces singularis* were also subjected to reactions so that the production of GOSs reached a yield of about 50%.

<Determination of the Degree of Polymerization>
  Column used: MCI™ GEL CK04S (Mitsubishi Chemical Corporation)
  Eluent: $H_2O$
  Flow rate: 0.4 ml/min
  Detector: RI
  Column temperature: 80° C.
<Determination of the Degree of Branching>
  Column used: Shodex (registered trademark) Asahipak NH2P-40 3E (Showa Denko K.K.)
  Eluent: MeCN:$H_2O$=75:25 (vol:vol)
  Flow rate: 0.35 ml/min
  Detector: RI
  Column temperature: 25° C.

(2) Results

Measurements results were used to calculate the content (%) of galacto-oligosaccharides (GOSs) in the total amount of sugars (total sugar), contained in the respective reaction solutions and the proportions (%) of respective GOSs with the indicated degrees of polymerization, at the indicated reaction temperatures (FIG. 6). The purified enzyme (wild-type strain enzyme) was found to have excellent GOS-producing ability. In addition, the wild-type strain enzyme was found to exhibit high levels of transglycosylation activity under high temperature conditions, and can be useful for the production of oligosaccharides.

Measurements results were used to calculate the proportions (%) of respective GOSs with the indicated degrees of polymerization. The results (typical results) for the degrees of polymerization of GOSs when the purified enzyme (wild-type strain enzyme) was used are shown in FIG. 7, upper table. The wild-type strain enzyme (*Cryptococcus terrestris* derived enzyme) was found to have excellent GOS-producing ability and to efficiently produce oligosaccharides, particularly trisaccharides and higher saccharides.

Measurements results were used to calculate the proportions (%) of linear and branched oligosaccharide in the resultant trisaccharides and to compare the ratios of trisaccharides with branched chain (i.e. the degrees of branching of trisaccharides) between the enzymes derived from *Cryptococcus terrestris* and known other β-galactosidase-producing strains. The results for the degrees of branching of GOSs when the purified enzyme (wild-type strain enzyme) was used are shown in FIG. 7, lower table. The wild-type strain enzyme (*Cryptococcus terrestris* derived enzyme) was found to produce predominantly linear oligosaccharides. Thus, it was revealed that the wild-type strain enzyme has transglycosylation activity in which the sugar chain is specifically transferred via β-1,4-glycosidic linkage and in particular, is less capable of transglycosilating so as to form β-1,6-glycosidic linkage.

6. Obtainment of β-Galactosidase Enzymes Produced by Mutant Strains, and Determination of Amino Acid Sequences and Molecular Weights Thereof Two mutant strains (M2 and M6) were obtained from *Cryptococcus terrestris* strain MM13-F2171 by means of mutagenesis with UV treatment. β-Galactosidase enzymes produced by these mutant strains were purified in procedures similar to those described above under 1.(2). Strains M2 and M6 each were found to have a high ability to produce mutant strain enzymes 1 to 3; strain M2 was observed to have a particularly high ability to produce mutant strain enzyme 1, and strain M6 to produce mutant strain enzymes 2 and 3. *Cryptococcus terrestris* strain M2 was deposited at Dec. 10, 2015 at the Patent Microorganisms Depositary, National Institute of Technology and Evaluation, under the name of *Cryptococcus terrestris* APC-6431, to which the Accession Number NITE BP-02178 was assigned.

The amino acid sequences of the obtained purified enzymes, i.e., one enzyme derived from mutant strain M2 (mutant strain enzyme 1) and two enzymes derived from mutant strain M6 (mutant strain enzymes 2 and 3), were determined. First, N-terminal amino acid sequences of mutant strain enzymes 1 to 3 were determined using a protein sequencer (PPSQ-31A, SHIMADZU CORPORATION). Then, the cDNA sequence of the wild-type strain enzyme (SEQ ID NO: 5) was searched for the base sequence corresponding to the N-terminal amino acid sequence of each of the mutant strain enzymes, thereby to determine the cDNA sequence encoding each of the mutant strain enzymes. The amino acid sequence of mutant strain enzyme 1 (SEQ ID NO: 2) corresponds to one having a deletion of the N-terminal 130 amino acid residues of the full-length amino acid sequence of the wild-type strain enzyme (SEQ ID NO: 1), which is deduced from the cDNA sequence encoding the wild-type strain enzyme (SEQ ID NO: 5). Similarly, the amino acid sequence of mutant strain enzyme 2 (SEQ ID NO: 3) corresponds to one having a deletion of the N-terminal 136 amino acid residues of the full-length amino acid sequence of the wild-type strain enzyme (SEQ ID NO: 1), while the amino acid sequence of mutant strain enzyme 3 (SEQ ID NO: 4) corresponds to one having a deletion of the N-terminal 141 amino acid residues of the full-length amino acid sequence of the wild-type strain enzyme (SEQ ID NO: 1).

Figure 8:
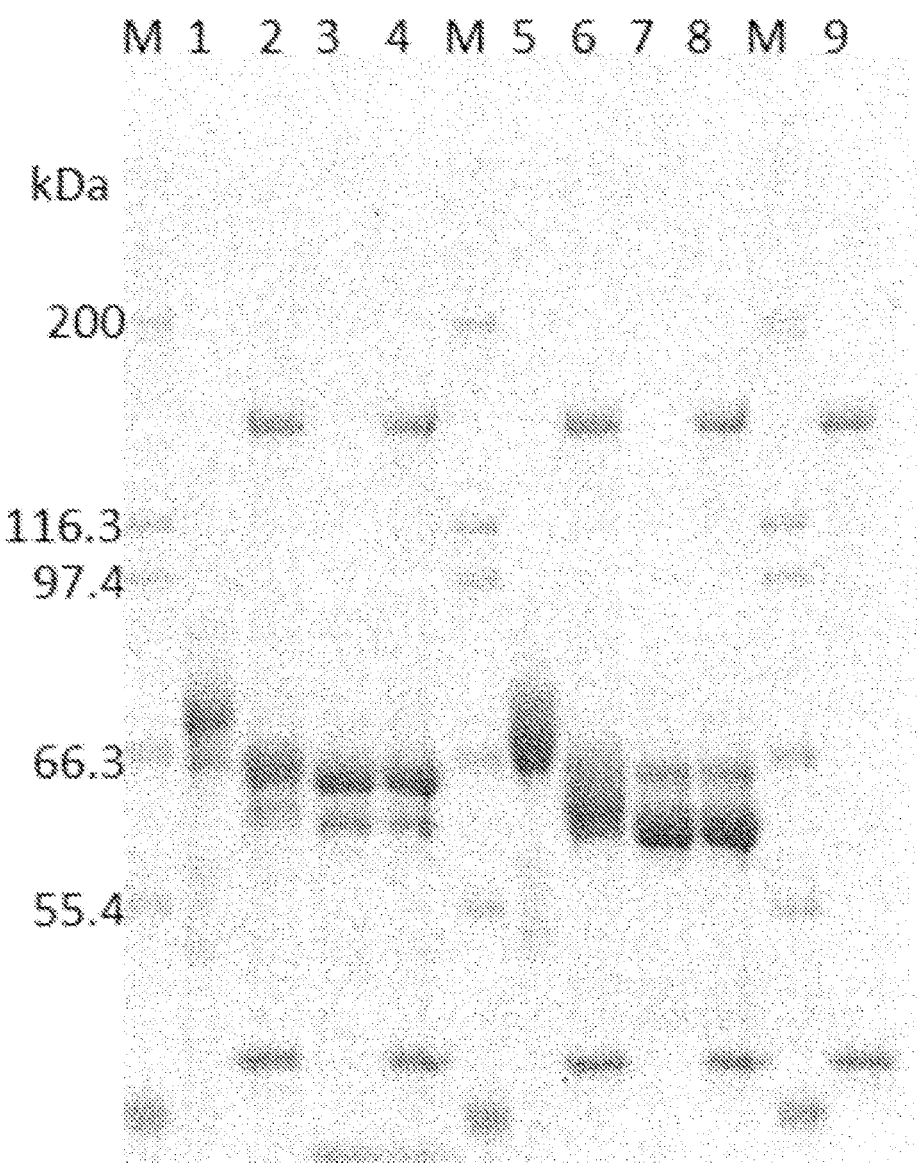
FIG. 8 shows results of determination of the molecular weights (by SDS-PAGE) of mutant strain enzymes derived from *Cryptococcus terrestris* strains M2 and M6. Lanes 1 to 4 represent the results for a mutant strain enzyme derived from *Cryptococcus terrestris* strain M2. M: molecular weight markers; Lane 1: no treatment; Lane 2: after treatment with O-glycosidase and neuraminidase; Lane 3: after treatment with PNGase F; Lane 4: after treatment with O-glycosidase, neuraminidase, and PNGase F. Lanes 5 to 8 represent the results for a mutant strain enzyme derived from *Cryptococcus terrestris* strain M6. Lane 5: no treatment; Lane 6: after treatment with O-glycosidase and neuraminidase; Lane 7: after treatment with PNGase F; Lane 8: after treatment with O-glycosidase, neuraminidase, and PNGase F.

Subsequently, the molecular weights of these mutant strain enzymes were determined by SDS-PAGE. Procedures and conditions for removing sugar chains were in accordance with those described above under 1.(2). The results of SDS-PAGE are shown in FIG. 8. In the following, there are shown the molecular weights of the respective mutant strain enzymes when the enzymes were subjected to no treatment, and treatments for removal of N-linked sugar chains, O-linked sugar chains, and both N-linked and O-linked sugar chains. On the basis of the results of SDS-PAGE analysis, it can be observed that strain M2 produces mutant strain enzymes 2 and 3, in addition to mutant strain enzyme 1.

<No Treatment>
  Mutant strain enzyme 1 (lanes 1 and 5): 71 kDa
  Mutant strain enzyme 2 (lanes 1 and 5): 66 kDa
  Mutant strain enzyme 3 (lanes 1 and 5): 66 kDa
<After Removal of O-Linked Sugar Chains>
  Mutant strain enzyme 1 (lanes 2 and 6): 65 kDa
  Mutant strain enzyme 2 (lanes 2 and 6): 63 kDa
  Mutant strain enzyme 3 (lanes 2 and 6): 62 kDa
<After Removal of N-Linked Sugar Chains>
  Mutant strain enzyme 1 (lanes 3 and 7): 64 kDa
  Mutant strain enzyme 2 (lanes 3 and 7): 61 kDa
  Mutant strain enzyme 3 (lanes 3 and 7): 61 kDa
<After Removal of Both O-Linked and N-Linked Sugar Chains>
  Mutant strain enzyme 1 (lanes 4 and 8): 64 kDa
  Mutant strain enzyme 2 (lanes 4 and 8): 61 kDa
  Mutant strain enzyme 3 (lanes 4 and 8): 61 kDa

7. Examination on Oligosaccharide Production Ability 2

(1) Methods

To aliquots of a lactose solution was added the purified enzyme derived from strain M2 (mutant strain enzyme 1) or M6 (mutant strain enzyme 3), and the mixtures were subjected to reaction. Examinations were performed for the degrees of polymerization and branching of sugars contained in the reaction solutions after the reaction was completed. The reaction conditions and measurements of the degrees of polymerization and branching were in accordance with those described above under 5.

(2) Results

Measurements results were used to calculate the content (%) of GOSs in the total amount of the sugars (total sugar) contained in the respective reaction solutions and the proportions (%) of respective GOSs with the indicated degrees of polymerization, at the indicated reaction temperatures (FIG. 9). The purified enzyme (mutant strain enzyme) was found to have excellent GOS-producing ability. In addition, the mutant strain enzyme was found to exhibit high levels of sugar transfer activity under high temperature conditions, and can be useful for the production of oligosaccharides. It can also be found that there were no differences in GOS producing ability between the wild-type stain enzyme and the mutant strain enzyme.

Measurements results were used to calculate the proportions (%) of respective GOSs with the indicated degrees of polymerization. The results (typical results) for the degrees of polymerization of GOSs when the purified mutated enzymes derived from strains M2 (mutant strain enzyme 1) and M6 (mutant strain enzyme 3) were used are shown in FIG. 10, upper table. The mutant strain enzymes were found to have excellent GOS-producing ability and to efficiently produce oligosaccharides, particularly trisaccharides and higher saccharides. It can also be found that there were no differences in GOS producing ability between the wild-type stain enzyme and the mutant strain enzymes.

Measurements results were used to calculate the proportions (%) of linear and branched oligosaccharide in the resultant trisaccharides and to compare the ratios of trisaccharides with branched chain (i.e. the degrees of branching of trisaccharides) between the wild-type strain enzymes and two mutant strain enzymes (FIG. 10, lower table). The mutant strain enzymes (mutated, *Cryptococcus terrestris* derived enzymes) were found to produce predominantly linear oligosaccharides. Thus, it was revealed that the mutant strain enzymes have transglycosilation activity in which the sugar chain is specifically transferred via β-1,4-glycosidic linkage and in particular, is less capable of transglycosilating so as to form β-1,6-glycosidic linkage. It was also observed that the wild-type strain enzyme and the mutant strain enzymes have a comparable ability to produce GOSs and do not have any substantial differences in terms of properties as β-galactosidase. Mutant strain enzyme 2 is a β-galactosidase enzyme of which the amino acid sequence is shorter by six amino acid residues at the N terminus than that of mutant strain enzyme 1 and longer by five amino acid residues at the N terminus than that of mutant strain enzyme 3. Since it is apparent from the above results that an amino acid sequence in an N-terminal region does not affect enzymatic properties, it can be inferred that mutant strain enzyme 2 also have enzymatic properties equivalent to those of mutant strain enzymes 1 and 3.

8. Examinations of Properties of Mutant Strain Enzymes 1 and 3

The purified, mutated enzymes (see the above section described under 6.) were used to examine properties of mutant strain enzymes 1 and 3. The experimental methods were similar to those described for the wild-type strain enzyme (see the above section described under 4.).

(1) Optimum pH and pH Stability

Figure 11:
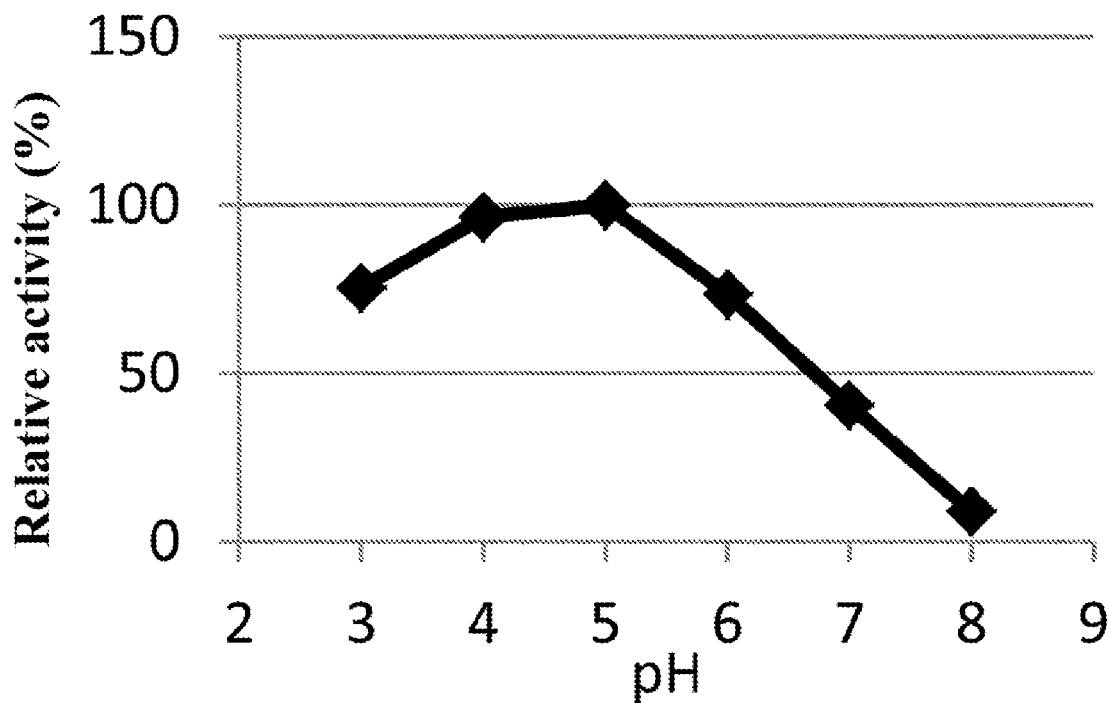
FIG. 11 is a graph showing the optimum pH of a purified enzyme (mutant strain enzyme 1).
Figure 12:
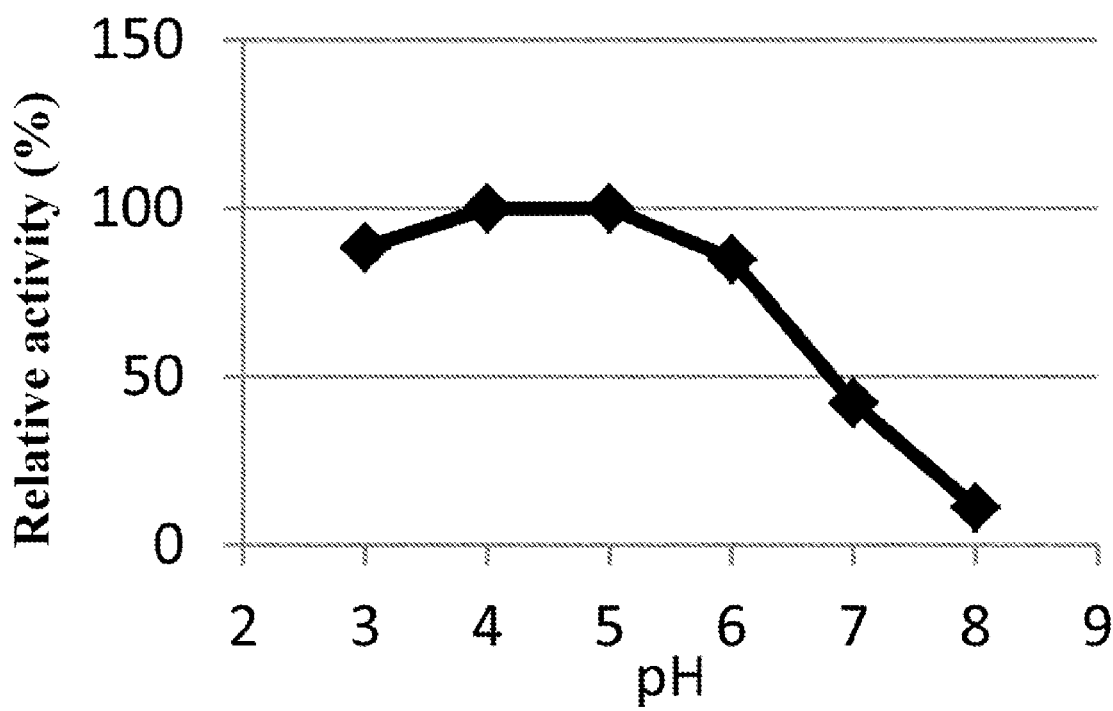
FIG. 12 is a graph showing the optimum pH of a purified enzyme (mutant strain enzyme 3).
Figure 13:
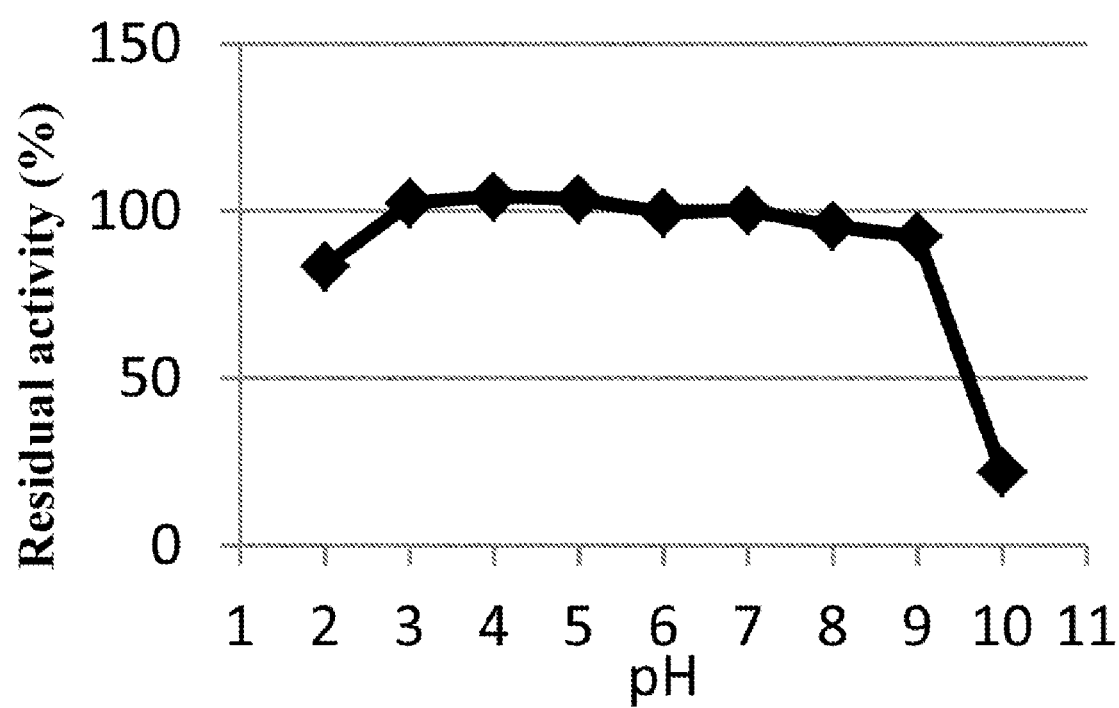
FIG. 13 is a graph showing the pH stability of a purified enzyme (mutant strain enzyme 1).
Figure 14:
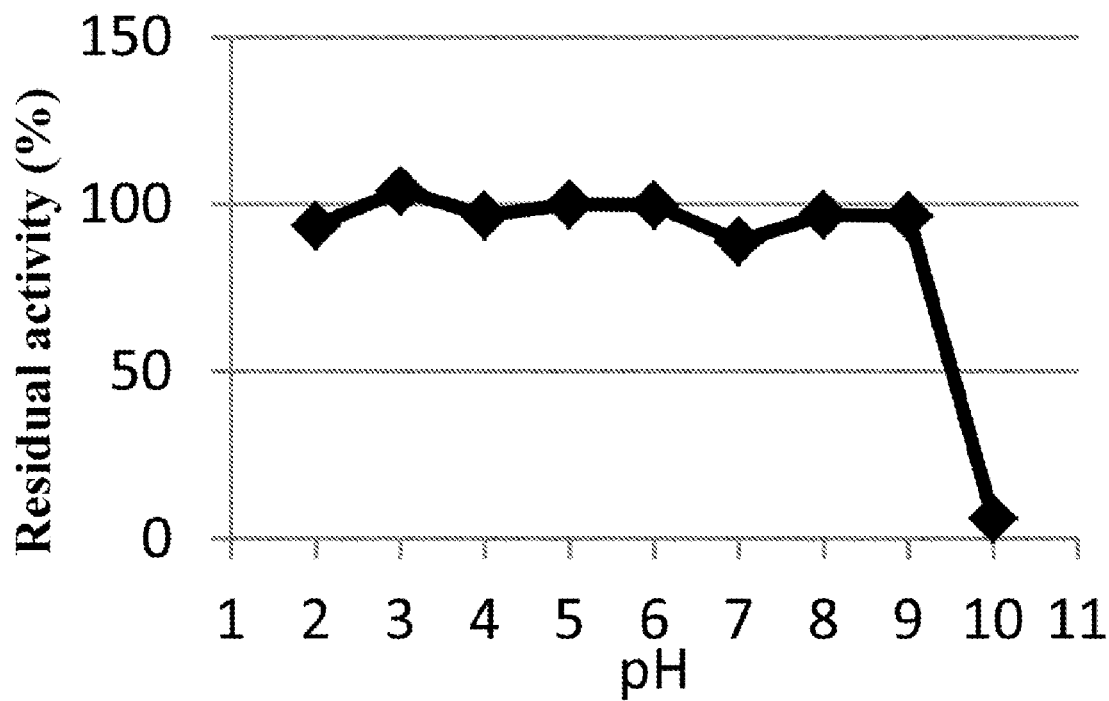
FIG. 14 is a graph showing the pH stability of a purified enzyme (mutant strain enzyme 3).

The results of measurements regarding optimum pH are shown in FIG. 11 (for mutant strain enzyme 1) and in FIG. 12 (for mutant strain enzyme 3). Mutant strain enzymes 1 and 3 each were found to have an optimum pH of 4 to 5. The results of measurements regarding pH stability are shown in FIG. 13 (for mutant strain enzyme 1) and in FIG. 14 (for mutant strain enzyme 3). Mutant strain enzymes 1 and 3 each were found to exhibit stable activity in the pH range of pH 2 to 9.

(2) Optimum Temperature and Thermostability

Figure 15:
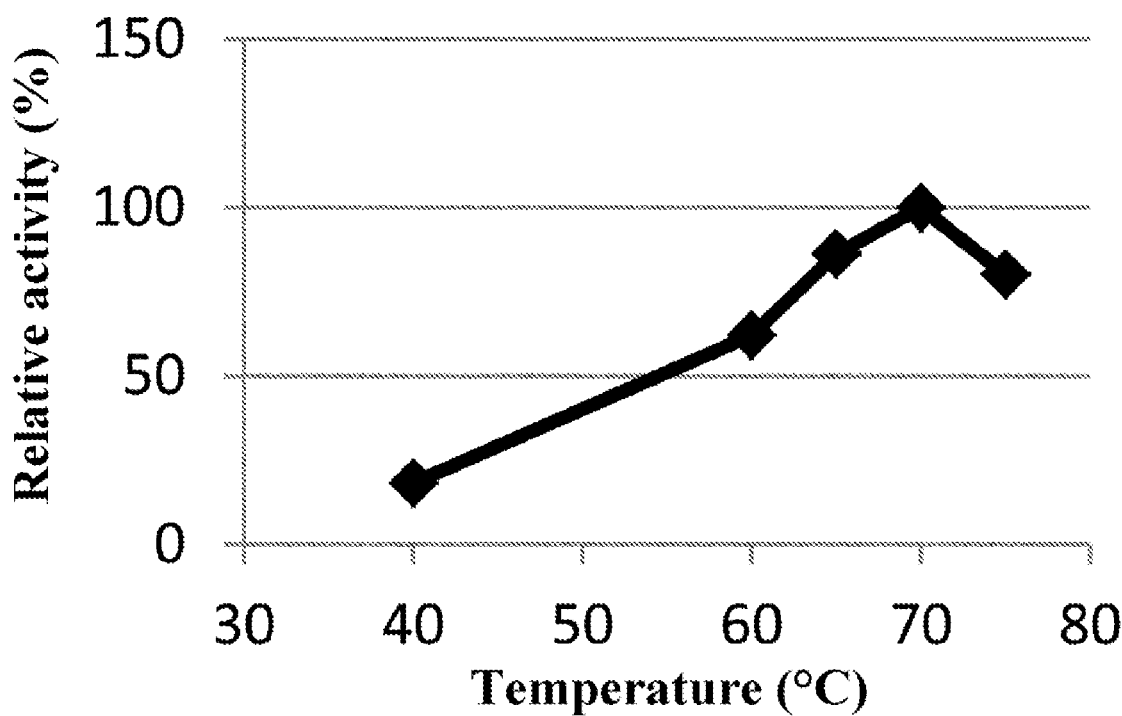
FIG. 15 is a graph showing the optimum temperature of a purified enzyme (mutant strain enzyme 1).
Figure 16:
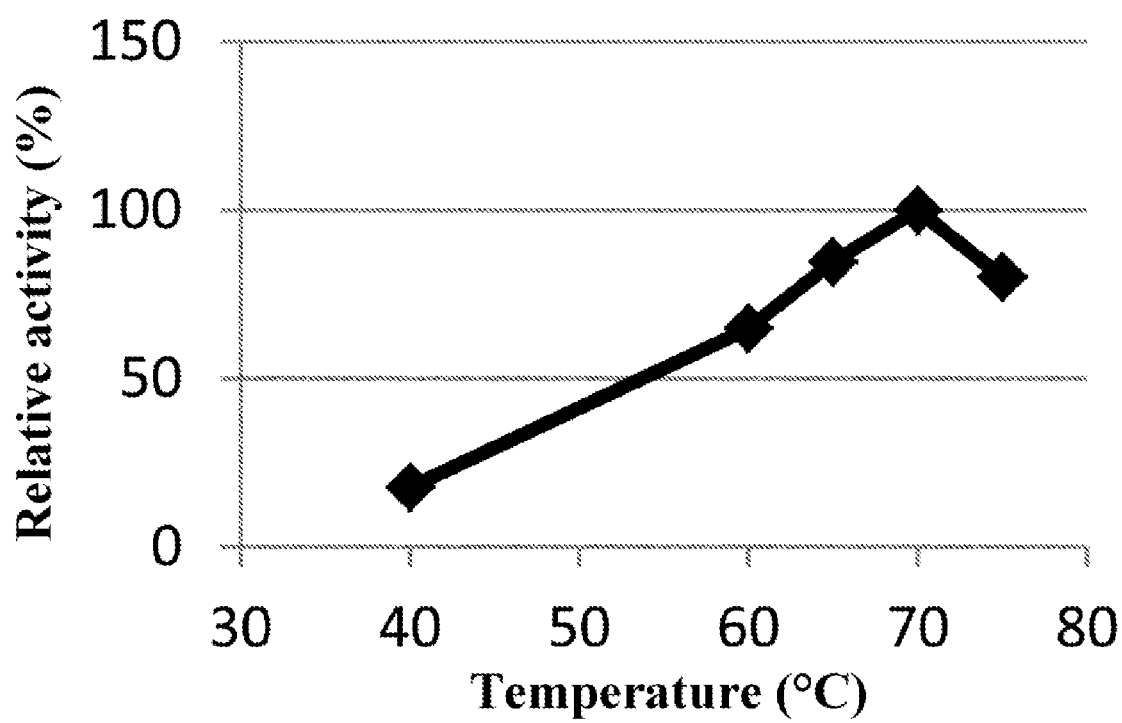
FIG. 16 is a graph showing the optimum temperature of a purified enzyme (mutant strain enzyme 3).
Figure 17:
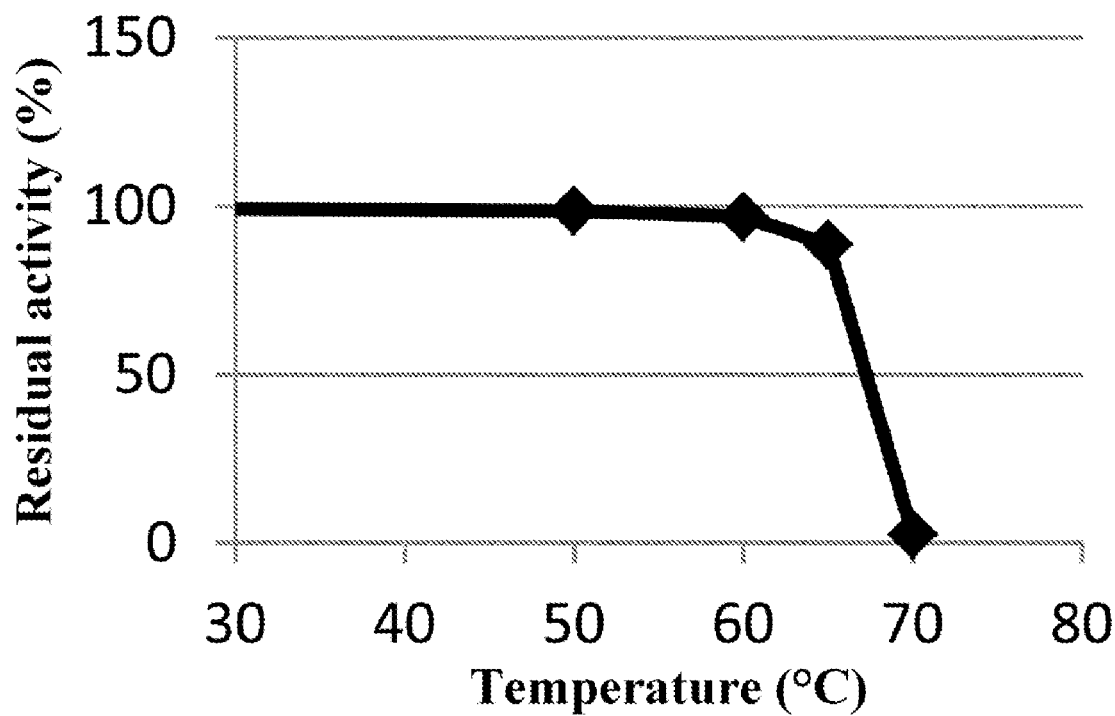
FIG. 17 is a graph showing the thermostability of a purified enzyme (mutant strain enzyme 1).
Figure 18:
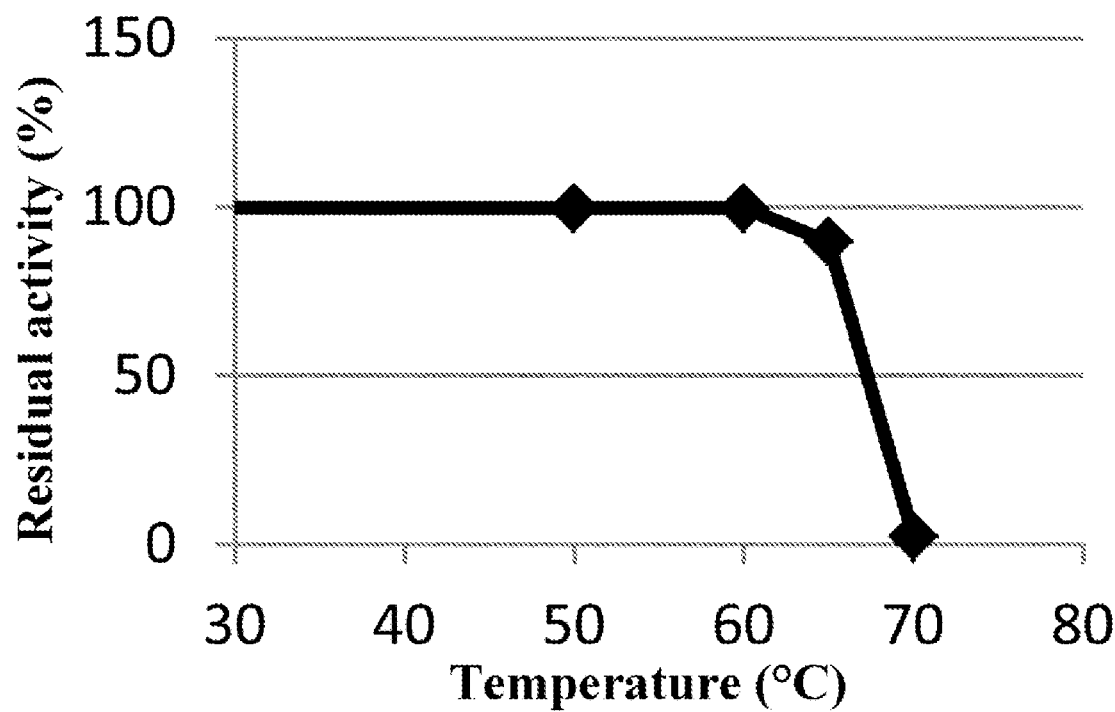
FIG. 18 is a graph showing the thermostability of a purified enzyme (mutant strain enzyme 3).

The results of measurements regarding optimum temperature are shown in FIG. 15 (for mutant strain enzyme 1) and in FIG. 16 (for mutant strain enzyme 3). Mutant strain enzymes 1 and 3 each were found to have an optimum temperature of 70° C. The results of measurements regarding thermostability are shown in FIG. 17 (for mutant strain enzyme 1) and in FIG. 18 (for mutant strain enzyme 3). Mutant strain enzymes 1 and 3 each were found to be stable between 30° C. and 65° C. and to retain enzyme activity at levels of 80% or more of the activity.

INDUSTRIAL APPLICABILITY

The present invention provides a novel β-galactosidase enzyme useful particularly for the production of oligosaccharides. The β-galactosidase enzyme of the present invention is useful, for example, for the purpose of producing galacto-oligosaccharides with a high content of linear oligosaccharides.

The present invention should not be limited in any way to the description of the embodiments and examples of the above-described invention. The present invention also includes a variety of modified embodiments within the scope that one skilled in the art could easily arrive without departing from the description of the scope of claims. The contents of the articles, published patent applications, patent publications, and others that are expressly provided in the specification are incorporated in their entire contents by citation.

The invention claimed is:

1. A method for producing galacto-oligosaccharides using a β-galactosidase enzyme, comprising:
administering a β-galactosidase enzyme to a raw material to form a mixture,
wherein the β-galactosidase enzyme comprises an amino acid sequence that is at least 90% identical to an amino acid sequence of any one of SEQ ID NOs: 1 to 4, and
wherein the raw material comprises lactose for producing galacto-oligosaccharides.

2. The method according to claim 1, further comprises:
preheating the raw material before the administering step of the β-galactosidase enzyme;
wherein the preheated raw material comprises about one liter solution containing 30% to 65% lactose; and the β-galactosidase administered ranges between about 75 U to 5000 U.

3. The method according to claim 2:
wherein the mixture is allowed to react at 30° C. to 75° C. for 15 to 50 hours,
thereby to result in the generation of galacto-oligosaccharides.

4. The method according to claim 1, wherein the β-galactosidase enzyme contains at least one substitution modification relative to one of SEQ ID NOS: 1 to 4.

5. The method according to claim 1, wherein the amino acid sequence is an amino acid sequence that is 95% or more identical to the amino acid sequence of any one of SEQ ID NOS: 1 to 4.

6. The method according to claim 1, wherein the amino acid sequence consists of an amino acid sequence having a length equal to or less than that of the amino acid sequence of SEQ ID NO: 1.

7. The method according to claim 1, further comprising obtaining the β-galactosidase enzyme directly from *Cryptococcus terrestris*.

8. The method according to claim 7, wherein the *Cryptococcus terrestris* is *Cryptococcus terrestris* strain MM13-F2171 (Accession Number: NITE BP-02177) or APC-6431 (Accession Number: NITE BP-02178).

9. The method according to claim 1, further comprising obtaining the β-galactosidase enzyme from a microorganism having a recombinant DNA encoding the β-galactosidase enzyme.

10. The method according to claim 9, wherein the recombinant DNA comprises a nucleotide sequence of SEQ ID NOS: 5, 6, 7 or 8.

* * * * *